United States Patent
Chiang et al.

(10) Patent No.: US 10,016,748 B2
(45) Date of Patent: Jul. 10, 2018

(54) IRON-SULFUR COMPLEX AND METHOD FOR PRODUCING HYDROGEN USING THE SAME AS CATALYST

(71) Applicant: Academia Sinica, Taipei (TW)

(72) Inventors: Ming-Hsi Chiang, Taipei (TW); Yu-Chiao Liu, Taipei (TW); Kai-Ti Chu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 346 days.

(21) Appl. No.: 14/509,509

(22) Filed: Oct. 8, 2014

(65) Prior Publication Data

US 2015/0101936 A1 Apr. 16, 2015

Related U.S. Application Data

(60) Provisional application No. 61/889,546, filed on Oct. 11, 2013.

(51) Int. Cl.
*B01J 31/22* (2006.01)
*C25B 1/02* (2006.01)
*C07F 15/02* (2006.01)

(52) U.S. Cl.
CPC .............. *B01J 31/226* (2013.01); *C07F 15/02* (2013.01); *C25B 1/02* (2013.01); *B01J 2231/60* (2013.01); *B01J 2531/842* (2013.01)

(58) Field of Classification Search
CPC .................................. C25B 1/02; B01J 31/226
See application file for complete search history.

(56) References Cited

PUBLICATIONS

Felton et al., "Hydrogen Generation from Weak Acids: Electrochemical and Computational Studies of a Diiron Hydrogenase Mimic," J. Am. Chem. Soc. 2007, 129, p. 12521-12530.*

(Continued)

*Primary Examiner* — Nicholas A Smith
(74) *Attorney, Agent, or Firm* — Bacon & Thomas, PLLC

(57) ABSTRACT

This invention relates to an iron-sulfur complex that is capable of efficiently catalyzing formation of hydrogen, and a method for producing hydrogen using the complex as a catalyst. The iron-sulfur complex provided herein comprises: a structure of formula (I)

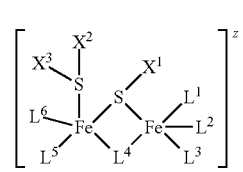

wherein the ligands $L^1$ to $L^3$, $L^5$ and $L^6$ and the groups $X^1$ to $X^3$ are each selected from the group consisting of alkyl, alkenyl, alkynyl and aryl that are substituted or unsubstituted, hydroxyl, carbonyl, aldehyde, and so on; $L^4$ is a bridging ligand selected from the group consisting of hydroxyl, carbonyl, and so on; and the symbol "z" means the charge, which is an integer with the range of −3 to +2. $X^1$ and $X^2$ may join together to form a bridging group between the two sulfur atoms. $X^3$ may alternatively be a vacant site.

4 Claims, 15 Drawing Sheets

| | | | |
|---|---|---|---|
| Fe(1)-Fe(2) | 2.6163(14) Å | Fe(2)-S(2) | 3.836 Å |
| Fe(1)-S(1) | 2.246(2) Å | Fe(1)-P | 2.183(2) Å |
| Fe(1)-S(2) | 2.302(2) Å | Fe(2)-P | 2.213(2) Å |
| Fe(2)-S(1) | 2.319(2) Å | | |

(56) References Cited

PUBLICATIONS

Triflate. (https://web.archive.org/web/20120525142205/https://en.wikipedia.org/wiki/Trifluoromethanesulfonate).*
Capon et al., Coordination Chemistry Reviews 253 (2009) pp. 1476-1494.*
Yu-Chiao Liu et al., "[FeFe] hydrogenase active site modeling: a key intermediate bearing a thiolate proton and Fe hydride", Chem. Commun., 2013, 49, 4743-4745.
Philip E. Rakita, "Triflic acid and its derivatives, a family of useful reagents for synthesis", Chimica oggi, 22 (3):48-50,—Mar. 2004.

* cited by examiner

| Fe(1)-Fe(2) | 2.6163(14) Å | Fe(2)-S(2) | 3.836 Å |
| Fe(1)-S(1) | 2.246(2) Å | Fe(1)-P | 2.183(2) Å |
| Fe(1)-S(2) | 2.302(2) Å | Fe(2)-P | 2.213(2) Å |
| Fe(2)-S(1) | 2.319(2) Å | | |

| Fe(1)-Fe(2) | 2.6134(7) Å | Fe(2)-S(2) | 2.3038(10) Å |
| Fe(1)-S(1) | 2.2888(9) Å | Fe(1)-P | 2.395(10) Å |
| Fe(1)-S(2) | 3.880 Å | Fe(2)-P | 2.2160(10) Å |
| Fe(2)-S(1) | 2.2453(9) Å | | |

IRON-SULFUR COMPLEX AND METHOD FOR PRODUCING HYDROGEN USING THE SAME AS CATALYST

TECHNICAL FIELD

This invention relates to hydrogen production, and particularly to an iron-sulfur complex that is capable of efficiently catalyzing formation of hydrogen, and a method for producing hydrogen using the complex as a catalyst.

BACKGROUND

Taking the adventures of clean and sustainable, hydrogen has emerged as potential energy carriers for addressing the energy consumption problem. How to obtain the fuel has already been a vital issue in the decade. Among several methods, electrolysis provides an efficient way to convert electricity into chemical bonds. In industry applications, platinum is used as working electrodes for hydrogen production. However, its high cost and energy inefficiency limit the widespread application and encourages people to seek for earth-abundant elements as substitutes as well as highly efficient catalysts for hydrogen evolution reaction (HER).

In nature, [FeFe]hydrogenase enzymes have catalytic efficiency of 6000-9000 molecules of molecular hydrogen per second (Frey, M. *Chembiochem* 2002, 3, 153). The active site of [FeFe]hydrogenase is composed of a diiron unit with ligation of carbonyl, cyanide, a dithiolate linker and a [4Fe4S] cluster. Intensive synthetic study on modeling complexes has been performed to mimic the active site of [FeFe]hydrogenase in order to replicate the catalytic ability for hydrogen production. FIG. 1 is a schematic diagram that summarizes several types of biomimetic models to the active site of [FeFe]hydrogenase via modification of redox sub-units, ligands and sub-site structures. For instance, the attached [4Fe4S] cluster is replaced by an artificial redox active unit to enhance the electron communication between the diiron core and the protein backbone (Type 1). The dithiolate bridge is substituted by different abiological analogs (Type 2). The first coordination sphere about the Fe center is replicated by coordination of σ-donating ligands. The bridgehead atom is changed from nitrogen to carbon, oxygen or other chalcogen atoms (Type 3). A vacant site, an iron-hydride and a bridging/semi-bridging CO group are key structural features in intermediates (Types 4-6). These synthetic approaches are employed to improve the performance of electrocatalysis for hydrogen formation. The catalytic efficiency unfortunately remains low albeit these studies have been investigated for over a decade. In 2012, Rauchfuss et al. reported a diiron thiolate complex that reveals a high turnover frequency (TOF) of 58,000 s$^{-1}$ (Carroll, M. E.; Barton, B. E.; Rauchfuss, T. B.; Carroll, P. J. *J. Am. Chem. Soc.* 2012, 134, 18843).

In addition, several homogeneous electrocatalysts, such as nickel, cobalt, and molybdenum complexes, have been developed for the purpose of the production of hydrogen. The highest TOF number of 106,000 of H$_2$ per second is reported by DuBois et al. in 2011. A synthetic nickel complex is employed in the presence of medium strength acids ([(DMF)H]OTf, pK$_a$=6.1 in acetonitrile) as proton sources (Helm, M. L.; Stewart, M. P.; Bullock, R. M.; DuBois, M. R.; DuBois, D. L. *Science* 2011, 333, 863).

SUMMARY

In view of the foregoing, this invention provides an iron-sulfur complex that is capable of efficiently catalyzing formation of hydrogen.

This invention also provides a method for producing hydrogen using the iron-sulfur complex of this invention as a catalyst.

The iron-sulfur complex provided herein comprises: a structure of formula (I)

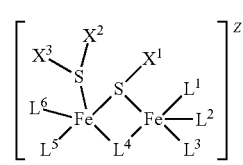

wherein

Z is a charge selected from an integer of −3 to +2; L1, L2, L3, L5, L6, X1, or X2 is a substituted or an unsubstituted functional group selected from the group consisting of: alkyl, alkenyl, alkynyl, phenyl, benzyl, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, orthocarbonate ester, carboxamide, primary amine, secondary amine, tertiary amine, primary ketimine, secondary ketimine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, phosphino, phosphono, phosphate, borono, boronate, borino, borinate and halogen;

L4 is a bridging ligand selected from the group consisting of hydroxyl, carbonyl, cyanide, primary amide, secondary amide, sulfide, disulfide, sulfinyl, thiolate, phosphide, halide, oxide, nitride, borylene, boryl, boride and hydride; and X3 is a vacant site or a substituted or an unsubstituted functional group selected from the group consisting of: alkyl, alkenyl, alkynyl, phenyl, benzyl, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, orthocarbonate ester, carboxamide, primary amine, secondary amine, tertiary amine, primary ketimine, secondary ketimine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, phosphino, phosphono, phosphate, borono, boronate, borino, borinate and halogen.

In some embodiments, X1 and X2 may be substituents within one bridging group. For example, the iron-sulfur complex may be a compound having a structure of formula (I-1)

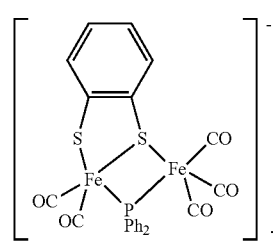

In some embodiments, the Fe atoms in the structure of formula (I) may be further connected with each other directly or indirectly.

For example, the iron-sulfur complex may be a compound having a structure of formula (I-2)

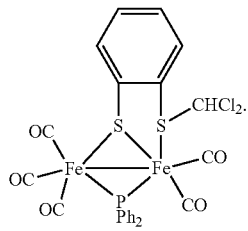

I-2

In some embodiments, the Fe atoms in the structure of formula (I) are connected with each other through a Fe—X—Fe bond, wherein X may include: H, halides CO, but not limited to this. In an exemplary embodiment, the iron-sulfur complex may be a compound having a structure of formula (I-3)

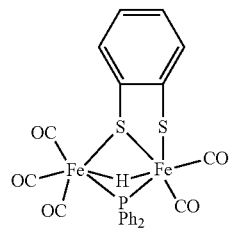

I-3

An iron-sulfur complex is also provided, comprising: a structure of formula (II),

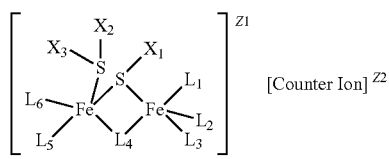

[Counter Ion]$^{Z2}$ wherein Z1 and Z2 are individually a charge selected from an integer of −3 to +2 but not 0.

the [counter ion]$^{Z2}$ comprises: K$^+$(L7)$_n$, Na$^+$(L7)$_n$, Li$^+$(L7)$_n$, [n-Bu$_4$N]$^+$, [PPN]$^+$, or [CF$_3$SO$_3$]$^-$, wherein L7 is a coordinating organic molecule, comprising: 18-crown-6-ether (1,4,7,10,13,16-hexaoxacyclooctadecane), 15-crown-5-ether (1,4,7,10,13-pentaoxacyclopentadecane), 12-crown-4-ether (1,4,7,10-tetraoxacyclododecane), or dibenzo-18-crown-6 (2,3,11,12-dibenzo-1,4,7,10,13,16-hexaoxacyclooctadeca-2,11-diene); or L7 is a coordinating solvent molecule, comprising: H$_2$O, THF or MeCN; and n is an integer selected from +1 to +13.

In some embodiments, X1 and X2 may be substituents within one bridging group.

In some embodiments, the Fe atoms in the structure of formula (II) may be further connected with each other directly or indirectly. Examples of the iron-sulfur complex may be a compound including any of following structures, but not limited to these:

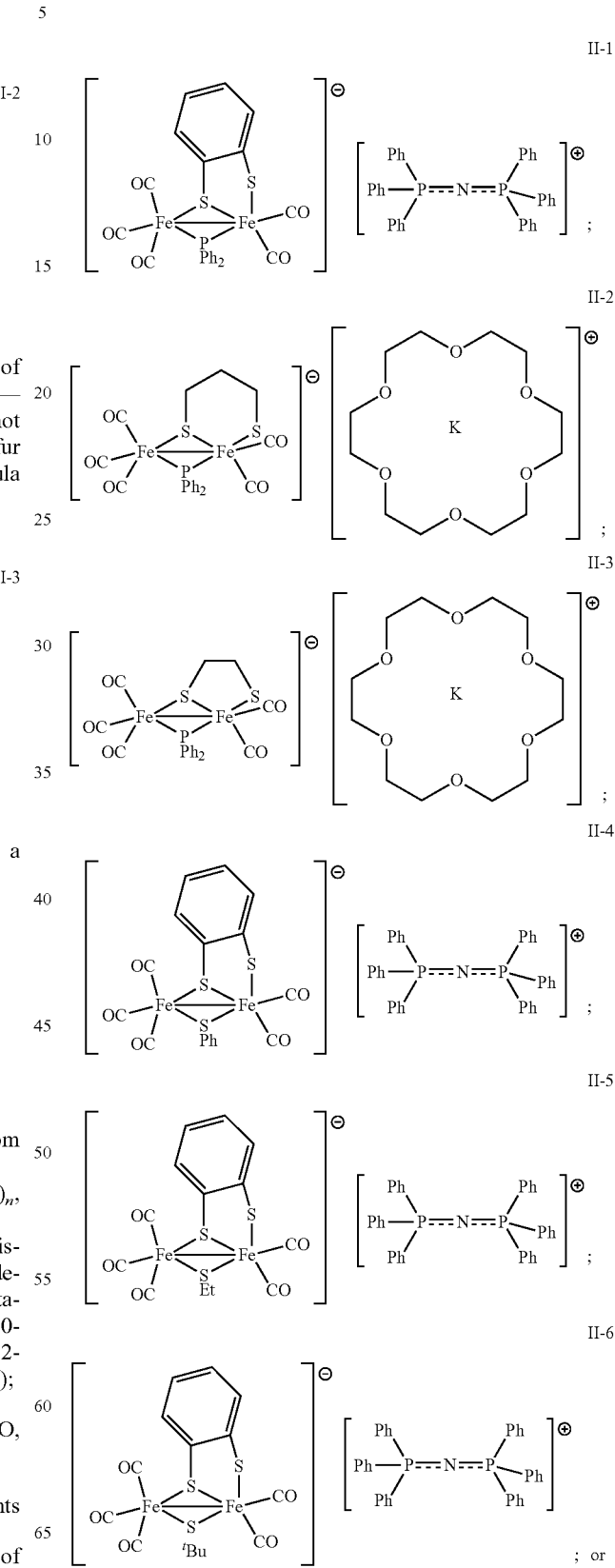

-continued

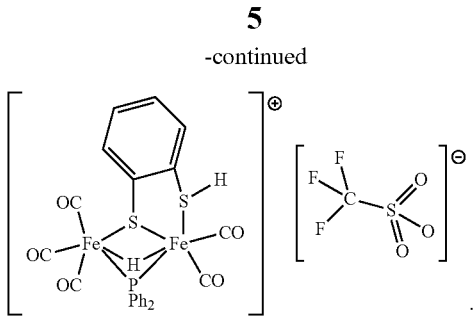

II-7

A method for producing hydrogen is also provided, comprising:

providing an electric potential to a proton-source substance in presence of the above iron-sulfur complex as a catalyst, whereby a proton in the proton-source substance is reduced to form hydrogen gas ($H_2$).

In some embodiments, the proton-source substance and the iron-sulfur complex are dissolved in a solvent to form a solution. In a preferred embodiment, the solution has a concentration of 0.5 M.

In some embodiments, examples of the solvent may include, but not limited to: acetonitrile, dichloromethane, tetrahydrofuran, acetone, or methanol. For example, the solvent may be an aqueous methanol solution.

In some embodiments, the proton-source substance has a concentration of 0.1 mM~1000 mM. In other embodiments, the iron-sulfur complex solution has a concentration of 0.1 mM~20 mM.

In some embodiments, examples of the proton-source substance may include: hydrochloric acid, anilinium acid, acetic acid, trifluoromethanesulfonic acid or methanol, but not limited to this.

In some embodiments, the proton-source substance may have a $pK_a$ of from −5 to +50.

As compared to the existing complexes in the prior art, the structural difference in which a terminal sulfur-containing ligand is coordinated to the Fe center leads to the tremendous catalytic efficiency for hydrogen production, which is discussed below.

Embodiments according to the inventive concept of the present invention are provided such that those skilled in the art can more completely understand the present invention. It should also be understood that the following embodiments are not limited by any of the details of the foregoing description, unless otherwise specified, but rather should be construed broadly within its spirit and scope as defined in the appended claims.

BRIEF DESCRIPTION OF THE DRAWING

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DESCRIPTION OF EMBODIMENTS

Preferred embodiments of the present invention will be described below in more detail with reference to the accompanying drawings. The present invention may, however, be embodied in different forms and should not be constructed as limited to the embodiments set forth herein. Other objectives, advantages, and novel features of the invention will become more apparent from the following detailed description when taken in conjunction with the accompanying drawings.

Embodiments of the inventive concept of the present invention may be modified in various forms, and the scope and spirit of the present invention should not be construed as being limited by the above-described embodiments. Therefore, the above-disclosed Embodiments are to be considered illustrative, and not restrictive, and the appended claims are intended to cover all such modifications, enhancements, and other embodiments, which fall within the true spirit and scope of the present invention.

[Structures of Iron-Sulfur Complexes Represented by Formula (I)]

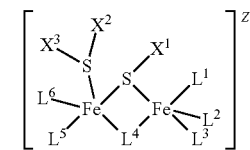

1. In an embodiment of this invention, the iron-sulfur complex represented by formula (I-1) has the following structural features: the ligands L$^1$, L$^2$, L$^3$, L$^5$ and L$^6$ are all CO, the bridging ligand L$^4$ is (μ-PPh$_2$)$^-$, the groups X$^1$ and X$^2$ join together to form a benzene ring as a bridging group between the two sulfur atoms, and X$^3$ is a vacant site. Such a complex can be expressed by [(μ-bdt)(μ-PPh$_2$)Fe$_2$(CO)$_5$]$^-$ or the following structural formula, wherein the term "bdt" means 1,2-benzenedithiolate.

I-1

2. In an embodiment of this invention, the iron-sulfur complex represented by formula (I-2) ([(μ-bdt-CHCl$_2$)(μ-PPh$_2$)Fe$_2$(CO)$_5$]) has the following structural features: In formula (I-2), two Fe centers are bridged by PPh$_2^-$ and one of the thiolate ends of the bdt ligand (bdt=1,2-benzenedithiolate). The other thiolate site is swung away from the Fe center. It is coordinated by a CHCl$_2$ group. Both bridging groups are asymmetrically coordinated to the metal sites.

I-2

3. In an embodiment of this invention, the iron-sulfur complex represented by formula (I-3) ([(μ-bdt)(μ-PPh$_2$)(μ-H)Fe$_2$(CO)$_5$]) has the following structural features: In formula (I-3), two Fe centers are bridged by PPh$_2^-$, one hydride group and one of the thiolate ends of the bdt ligand (bdt=1, 2-benzenedithiolate). The other thiolate site is swung away from the Fe center. All three bridging groups are asymmetrically coordinated to the metal sites.

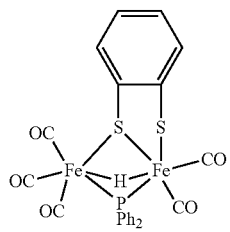

I-3

[Structures of Iron-Sulfur Complexes Represented by Formula (II)]

$$\begin{bmatrix} X_2 \\ X_3 \diagdown \mid \diagup X_1 \\ S \\ \diagup \diagdown \\ L_6 - Fe \underset{S}{\overline{\phantom{xx}}} Fe - L_1 \\ L_5 \diagup \mid \diagdown L_2 \\ L_4 \phantom{x} L_3 \end{bmatrix}^{Z1} \quad [\text{Counter Ion}]^{Z2}$$

Figure 1:
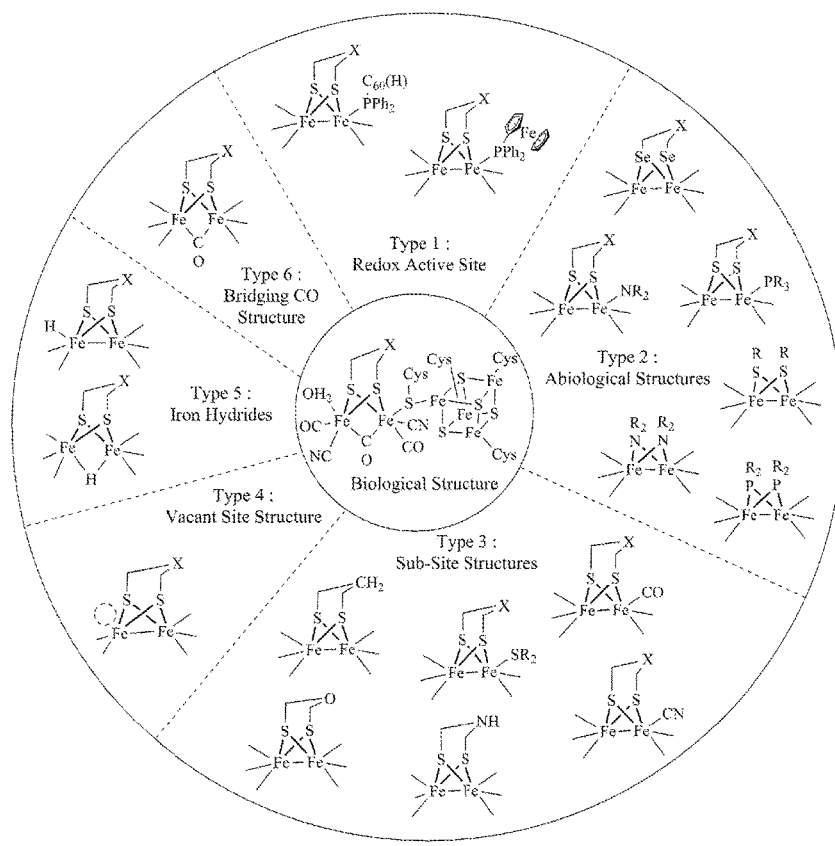
FIG. 1 illustrates the schematic diagram of the active site of [FeFe]hydrogenase and its biomimetic analogues in the prior art.
Figure 2:
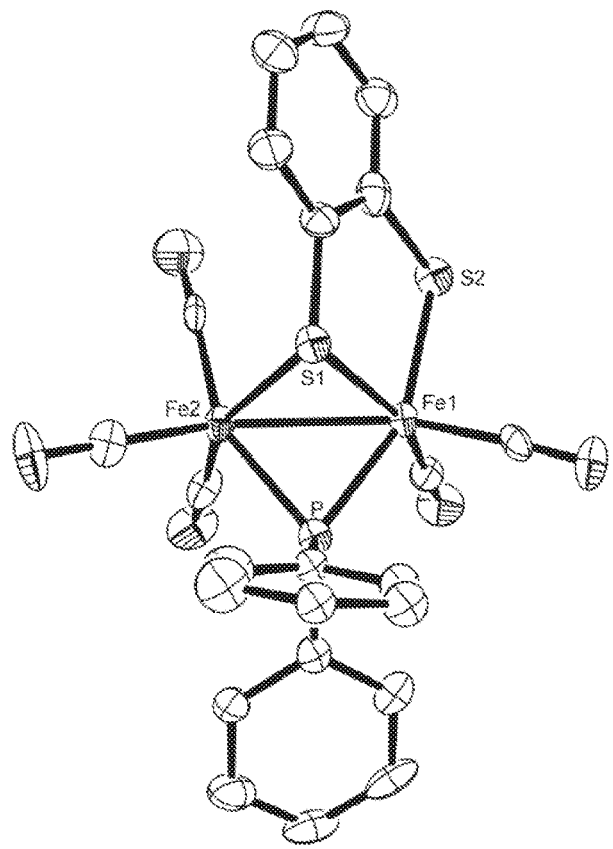
FIG. 2 shows the molecular structure for the anionic part of complex A-1 whose its cationic counterpart is omitted for clarity.

1. In an embodiment of this invention, the iron-sulfur complex represented by formula (II-1) ([PPN][(μ-bdt)(μ-PPh$_2$)Fe$_2$(CO)$_5$]) has the following structural features: In formula (II-1), two Fe centers are bridged by PPh$_2^-$ and one of the thiolate ends of the bdt ligand (bdt=1,2-benzenedithiolate). The other thiolate site is swung away from the Fe center. Both bridging groups are asymmetrically coordinated to the metal sites. The molecular structure for the anionic part of complex II-1 is shown in FIG. 2 and its cationic counterpart is omitted for clarity. The important bond distances are listed in the corresponding table in FIG. 2.

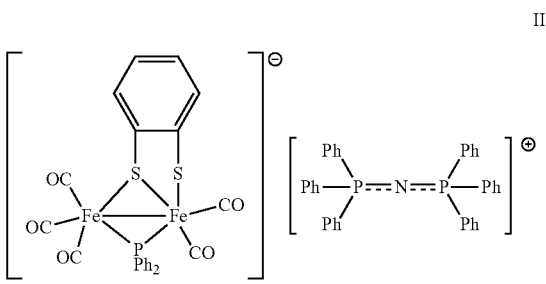

II-1

2. In an embodiment of this invention, the iron-sulfur complex II-2 represented by formula (II-2) ([K-18-crown-6-ether][(μ-pdt)(μ-PPh$_2$)Fe$_2$(CO)$_5$]) has the following structural features: In formula (II-2), two Fe centers are bridged by PPh$_2$ and one of the thiolate ends of the pdt ligand (pdt=1,3-propanedithiolate). The other thiolate site is swung away from the Fe center. Both bridging groups are asymmetrically coordinated to the metal sites.

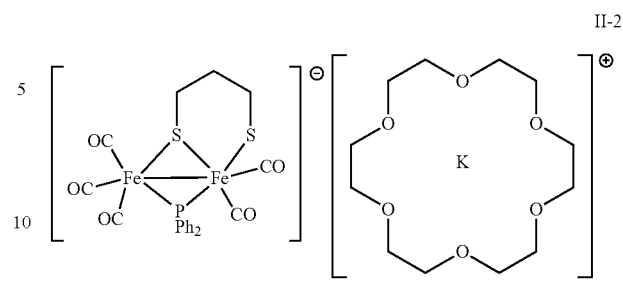

II-2

3. In an embodiment of this invention, the iron-sulfur complex II-3 represented by formula (II-3) [K-18-crown-6-ether][(μ-edt)(μ-PPh$_2$)Fe$_2$(CO)$_5$] has the following structural features: In formula (II-3), two Fe centers are bridged by PPh$_2$ and one of the thiolate ends of the edt ligand (edt=1,2-ethanedithiolate). The other thiolate site is swung away from the Fe center. Both bridging groups are asymmetrically coordinated to the metal sites.

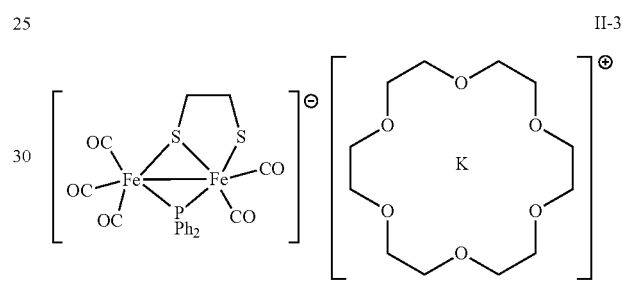

II-3

4. In an embodiment of this invention, the iron-sulfur complex II-4 represented by formula (II-4) [PPN][(μ-bdt)(μ-SPh)Fe$_2$(CO)$_5$] has the following structural features: In formula (II-4), two Fe centers are bridged by SPh$^-$ and one of the thiolate ends of the bdt ligand (bdt=1,2-benzenedithiolate). The other thiolate site is swung away from the Fe center. Both bridging groups are asymmetrically coordinated to the metal sites.

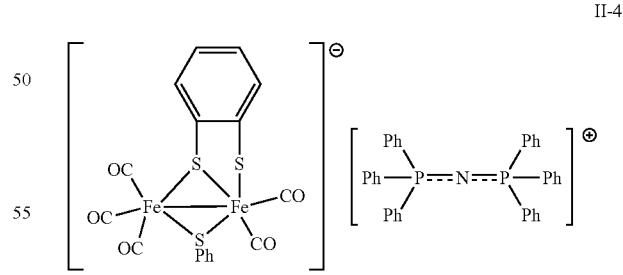

II-4

5. In an embodiment of this invention, the iron-sulfur complex represented by formula (II-5) [PPN][(μ-bdt)(μ-SEt)Fe$_2$(CO)$_5$] has the following structural features: In formula (II-5), two Fe centers are bridged by SEt$^-$ and one of the thiolate ends of the bdt ligand (bdt=1,2-benzenedithiolate). The other thiolate site is swung away from the Fe center. Both bridging groups are asymmetrically coordinated to the metal sites.

II-5

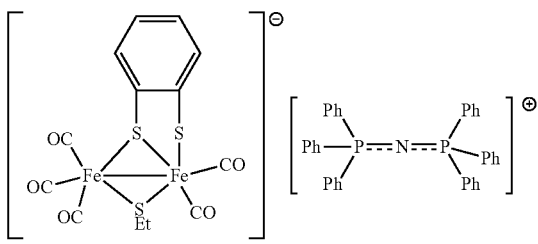

6. In an embodiment of this invention, the iron-sulfur complex II-6 represented by formula (II-6) [PPN][(μ-bdt)(μ-S$^t$Bu)Fe$_2$(CO)$_5$] has the following structural features: In formula (II-6), two Fe centers are bridged by S$^t$Bu$^-$ and one of the thiolate ends of the bdt ligand (bdt=1,2-benzenedithiolate). The other thiolate site is swung away from the Fe center. Both bridging groups are asymmetrically coordinated to the metal sites.

II-6

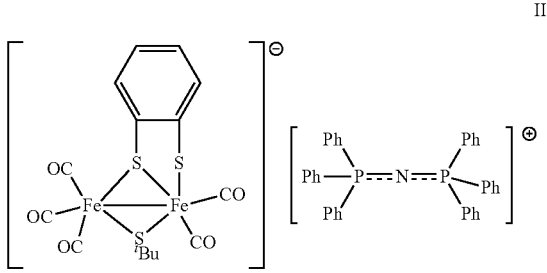

7. In an embodiment of this invention, the iron-sulfur complex II-7 represented by formula (II-7) [(μ-Hbdt)(μ-PPh$_2$)(μ-H)Fe$_2$(CO)$_5$][OTf] has the following structural features: In formula (II-7), two Fe centers are bridged by PPh$_2$$^-$, one hydride group and one of the thiolate ends of the bdt ligand (bdt=1,2-benzenedithiolate). The other thiolate site is swung away from the Fe center. It is coordinated by a proton. All three bridging groups are asymmetrically coordinated to the metal sites.

II-7

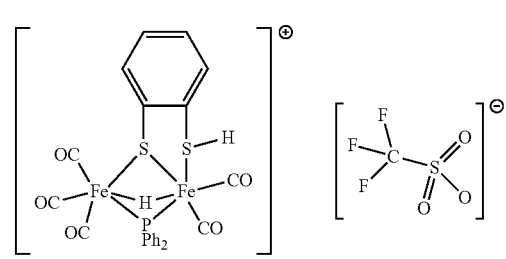

[Method for Producing Hydrogen Gas]

In the method for producing hydrogen gas, an electric potential is provided to a proton-source substance in presence of the iron-sulfur complex of this invention as a catalyst, such that the proton in the substance is reduced to form hydrogen gas (H$_2$).

Examples of the proton-source substance include: hydrochloric acid, anilinium acid, acetic acid, trifluoromethanesulfonic acid or methanol, but not limited to this.

The electrochemical reaction is usually conducted in a solution capable of dissolving the proton-source substance and the iron-sulfur complex or a salt of the iron-sulfur complex. Examples of the solvent include: acetonitrile, dichloromethane, tetrahydrofuran and aqueous methanol.

[Scheme 1: A General Synthesis Route for Complex A]

Because iron-sulfur complexes of formula (I) can be converted from those complexes of formula (II), scheme 1 herein only illustrates a synthesis route for complex A which has a structure of formula (II) from raw materials. The synthesis of complexes formula (II) will be further discussed in the following Preparing Examples and Scheme 2.

The method for producing a diiron thiolate complex represented by the scheme 1, a stereoisomer thereof, or a salt thereof is referred as a complex A and is not particularly limited. Any method can be used. Scheme 1 can be carried out in the following manner. The experimental details such as the solvent, the reaction temperature and the reaction time are illustrative examples. They are not limited to those described below and can be altered as appropriate.

Step 1 in the scheme 1 can be carried out by setting reaction conditions as appropriate with reference to, for example, Javier A. Cabeza, M. Angeles Martinez-Garcia, Victor Riera, Diego Ardura, and Santiago Garcia-Granda, *Organometallics* 1998, 17, 1471-1477 and the like, which are hereby incorporated by reference in its entirety. The following reaction was conducted under inert atmosphere. A solution of Fe$_3$(CO)$_{12}$ (complex 101, 1 equiv.) in tetrahydrofuran solution (or hexane, toluene solution) was treated with bidentate thiols (1 equiv.) or monodentate thiols (2 equiv.). The reaction mixture was then stirred at refluxing temperature for a period of time. The resulting dark colored mixture was evaporated to dryness in vacuo, and the crude product was purified by chromatography on silica gel with dichloromethane/hexane (v/v 1/1) as the eluent. From the red band, the product (complex 102) was obtained as a red solid.

Step 2 in the scheme 1 can be carried out by setting reaction conditions as appropriate with reference to, for example, Thomas B. Rauchfuss, Stephen M. Contakes, Sodio C. H. Hsu, Michael A. Reynolds, and Scott R. Wilson, *Journal of American Chemical Society*, 2001, 123, 6933-6934 or Ming-Hsi Chiang, Yu-Chiao Liu, Shu-Ting Yang, and Gene-Hsiang Lee, *Inorganic Chemistry* 2009, 48, 7604-7612 and the like, which are hereby incorporated by reference in its entirety. The following reaction was conducted under N$_2$. A solution of complex 102 (1 equiv.) in tetrahydrofuran solution (or hexane, dichloromethane solution) was treated with ligand L1 (1 equiv.). The reaction mixture was then stirred at 70° C. for 10 minutes or 25° C. for 1 hour. After the reaction, L2 (1 equiv.) was added to the solution. The substitution reaction was repeated as above. The complex 103 was obtained after 5 carbonyl groups were replaced. The reaction can also be performed by one-pot synthetic method. All ligands (L1, L2, L3, L5, L6, 1 equiv. each) were added into the reaction solution containing complex 102 in tetrahydrofuran solution (or hexane, dichloromethane solution). The decarbonylation occurred at 298 K for mono-substitution reaction. Multiple substitutions require reaction temperature higher than 373 K in toluene solution. The reaction was monitored via FTIR spectroscopy. The reaction was dried under vacuum once the substitution reaction was finished. The solid was washed by several portions of tetrahydrofuran/hexane (v/v 1/1) solution. A product (complex 103) was obtained.

Step 3-1 in the scheme 1 can be carried out by setting reaction conditions as appropriate with reference to, for example, Yu-Chiao Liu, Kai-Ti Chu, Ruei-Lin Jhang, Gene-Hsiang Lee and Ming-Hsi Chiang, *Chemical Communication* 2013, 49, 4743-4745 and the like, which is hereby incorporated by reference in its entirety. The following reaction was conducted under $N_2$. To a tetrahydrofuran solution of complex 102 or complex 103 (1 equiv.) was added $[L4]^{a+}$[counter ion]$^{a-}$ (1 equiv.) dissolved in the tetrahydrofuran solution. The resultant solution was allowed to stir overnight. The solution was filtered through Celite and was concentrated to a small volume. The product was precipitated upon addition of hexane. The solid was washed with hexane three times and then dried under vacuum. The product was isolated.

Step 3-2 in the scheme 1 can be carried out by setting reaction conditions as appropriate with reference to, for example, Yu-Chiao Liu, Ling-Kuang Tu, Tao-Hung Yen, Gene-Hsiang Lee, Shu-Ting Yang, and Ming-Hsi Chiang, *Inorganic Chemistry* 2010, 49, 6409-6420 and the like, which are hereby incorporated by reference in its entirety. The following reaction was conducted under $N_2$. To a solution of complex (1 equiv.) which was prepared from Step 3-1 in dichloromethane solution was added $[X3]^{b+}$ [counter ion]$^{b-}$ (1 equiv.). The solution was stirred for a period of time at room temperature and some precipitate appeared. The stirring was continued for additional time before the solvent volume was decreased to a small volume. Addition of diethyl ether led to precipitation of the solid. It was washed three times with dichloromethane/ether and dried in vacuo. The product complex A) was obtained.

All commercial available chemicals were of ACS grade and used without further purification. Solvents were of HPLC grade and purified as follows: diethyl ether and tetrahydrofuan were distilled from sodium/benzophenone under $N_2$. Hexane was distilled from sodium under $N_2$. Dichloromethane was distilled from $CaH_2$ under $N_2$. Acetonitrile was distilled first over $CaH_2$ and then from $P_2O_5$ under $N_2$. Deuterated solvents obtained from Merck were distilled over 4 Å molecular sieves under $N_2$ prior to use.

Infrared spectra were recorded on a Perkin-Elmer Spectrum One using a 0.05-mm $CaF_2$ cell. $^1H$, $^{13}C\{^1H\}$ and $^{31}P\{^1H\}$NMR spectra were recorded on a Bruker AV-500 or DRX-500 spectrometer operating at 500, 125.7, and 202.49 MHz, respectively. UV-vis spectra were recorded on a Varian Cary 5000 spectrophotometer using 1-cm cuvettes fitted with Teflon stoppers. Mass spectral analyses were done on a Waters LCT Premier XE. Elemental analyses were performed on an Elementar vario EL III elemental analyzer.

Electrochemical measurements were recorded on a CH Instruments 630C electrochemical potentiostat using a gastight three-electrode cell under $N_2$ at room temperature or at the specific temperature mentioned. A glassy carbon electrode and a platinum wire were used as working and auxiliary electrodes, respectively. The reference electrode was a non-aqueous $Ag/Ag^+$ electrode (0.01 M $AgNO_3$/0.1 M n-$Bu_4NPF_6$ or 0.4 M n-$Bu_4NPF_6$). All potentials are measured in 0.1 or 0.4 M n-$Bu_4NPF_6$ solution in dichloromethane or tetrahydrofuan. They are reported against ferrocenium/ferrocene ($Fc^+$/Fc). For electrocatalytic study of hydrogen production, increments of acids were added by

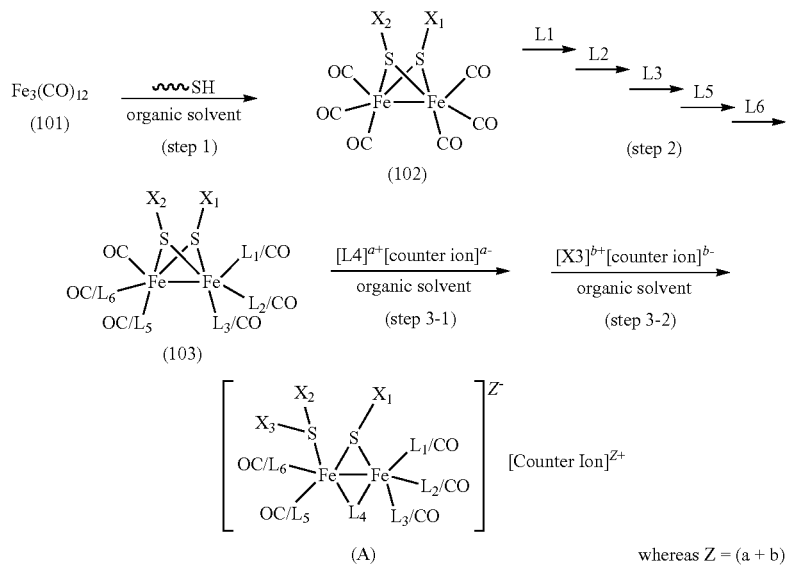

EXAMPLES

Some examples are provided below to further explain this invention, which are however not intended to restrict the scope of this invention.

Measurement Conditions

In the following examples, each reaction was characterized by the Infra-red spectroscopy, ESI-mass or FAB-mass spectroscopy, GC, $^1H$-/$^{13}C$-NMR (and $^{31}P$-NMR if required). All reactions were carried out by using standard Schlenk and vacuum-line techniques under an atmosphere of purified nitrogen.

microsyringe. Analysis of gas evolved from the electrochemical processes by GC (Agilent 7890 gas chromatograph with a TCD detector and a Restek ShinCarbon ST column. Nitrogen was used as the carrier gas) confirms hydrogen to be the sole content in the gaseous product.

Spectroelectrochemistry was performed by a Mettler Toledo ReactIR iC10 in situ FTIR system equipped with a MCT detector and a 0.625-in. SiComp probe. Graphite rods (6.15 mm in diameter) were used as working and auxiliary electrodes. Reference electrode was a non-aqueous $Ag/Ag^+$ electrode (0.01 M $AgNO_3$/0.1 M n-$Bu_4NPF_6$), which was placed in a separated compartment with a fine porosity glass frit. The solution was stirred under $N_2$ throughout bulk electrolysis. The X-ray single crystal crystallographic data collections were carried out at 150 K on a Bruker SMART APEX CCD four-circle diffractometer with graphite-monochromated Mo Kα radiation (λ=0.71073 Å) outfitted with a low-temperature, nitrogen-stream aperture.

The structures were solved using direct methods, in conjunction with standard difference Fourier techniques and refined by full-matrix least-squares procedures. An empirical absorption correction (multiscan) was applied to the diffraction data for all structures. All non-hydrogen atoms were refined anisotropically, and all hydrogen atoms were placed in geometrically calculated positions by the riding model. All software used for diffraction data processing and crystal structure solution and refinement are contained in the SHELXL-97 program suites.

Preparing Examples

Synthesis of Diiron Dithiolate Phosphine Complexes

A diiron dithiolate phosphine complex was synthesized according to the Scheme 2. This will be described specifically below.

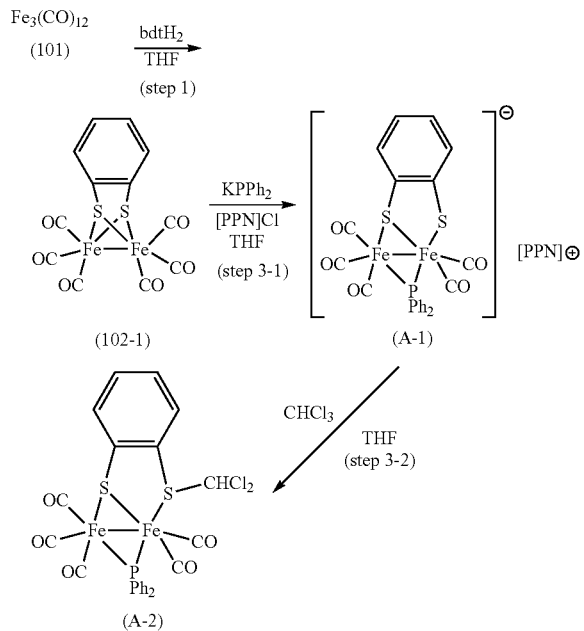

Preparing Example 1

Synthesis of [PPN][(μ-bdt)(μ-PPh$_2$)Fe$_2$(CO)$_5$] (complex A-1, which has the structure of formula (II-1)) and [(μ-bdt-CHCl$_2$)(μ-PPh$_2$)Fe$_2$(CO)$_5$] (complex A-2, which has the structure of formula (I-2))

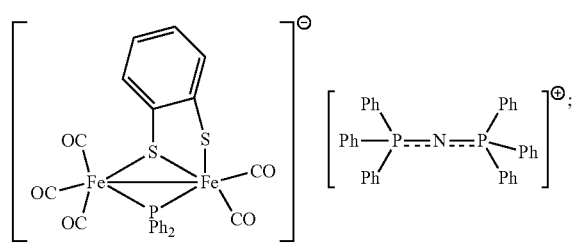

II-1

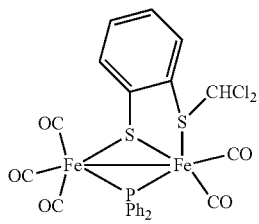

I-2

Step 1

Synthesis of [(μ-bdt)Fe$_2$(CO)$_6$] (complex 102-1)

To a solution of [Fe$_3$(CO)$_{12}$] (0.5 g, 1 mmol, complex 101) in tetrahydrofuan solution (15 mL) was added 1,2-benzenedithiol (127 μL, 1.1 mmol). The solution was stirred at reflux temperature for 1 hour to give a red solution. The solution was cooled down and filtered through Celite. The filtrate was dried under vacuo. The red solid was dissolved in hexane (5 mL). The crude product was purified by chromatography on silica gel with dichloromethane/hexane (v/v 1/1) as the eluent. From the red band, the product, [(μ-bdt)Fe$_2$(CO)$_6$] (complex 102-1), was obtained as a red solid (218 mg, 52%).

FTIR (vCO, hexane): 2079 m, 2043 s, 2006 vs, 1966 vw, 1957 vw cm$^{-1}$.

$^1$H NMR (500 MHz, CDCl$_3$): 7.11 (m), 6.62 (m) ppm.

Elementary analysis: Calcd for C$_{12}$H$_4$Fe$_2$O$_6$S$_2$: C, 34.32%; H, 0.96%. Anal. Found: C, 34.30%; H, 1.00%.

ESI-mass: m/z 420.1 (M$_+$).

Step 2

Synthesis of [(μ-bdt)Fe$_2$(CO)$_5$(PPh$_3$)] (complex 103)

As shown in Scheme 1 and 2, a Schlenk flask was charged with complex 102 synthesized in Step 1, namely, [(μ-bdt)Fe$_2$(CO)$_6$] (420 mg, 1 mmol, complex 102-1), and PPh$_3$ (384 mg, 1 mmol) in toluene (40 mL). The solution was refluxed for 1 h, and the solvent was then removed under reduced pressure after cooled to room temperature. The crude product was purified by chromatography on silica gel, eluting first with dichloromethane/hexane (v/v 1/4) to remove any unreacted starting materials, then with dichloromethane to elute the product. [(μ-bdt)Fe$_2$(CO)$_5$(PPh$_3$)] (complex 103) was obtained as a red solid in 70% yield (458 mg) after removal of solvent.

FTIR (vCO, CH$_2$Cl$_2$): 2044 s, 1981 vs, 1958 sh, 1924 w cm$^{-1}$.

$^1$H NMR (500 MHz, CD$_2$Cl$_2$): 7.46 (m), 7.55 (m) ppm.

$^{31}$P{$^1$H} NMR (202.48 MHz, CD$_2$Cl$_2$): δ1.45 ppm.

Elementary analysis: Calcd for C$_{29}$H$_{19}$Fe$_2$O$_5$PS$_2$: C, 53.24%; H, 2.93%. Anal. Found: C, 53.11%; H, 2.78%.

ESI-mass: m/z 654.5 (M+).

Step 3-1

Synthesis of [PPN][(μ-bdt)(μ-PPh$_2$)Fe$_2$(CO)$_5$] (complex A-1)

To a red tetrahydrofuan solution (50 mL) of [(μ-bdt)Fe$_2$(CO)$_6$] (600 mg, 1.429 mmol, complex 102-1) was added 0.5 M KPPh$_2$ (2.86 mL, 1.43 mmol) in the tetrahydrofuan solution. The brown solution was allowed to stir overnight. The solution was filtered through Celite and was concentrated to a small volume. The product was precipitated upon addition of hexane. The dark green-brown solid was washed with 40 mL of hexane three times and then dried under vacuum. The green-brown solution was dissolved in 30 mL of acetone, followed by addition of 820 mg (1.429 mmol) of bis(triphenylphosphine)iminium chloride ([PPN]Cl). The reaction mixture was stirred at room temperature for 3 h and the solvent was removed in vacuo. The residue was dissolved in 20 mL of tetrahydrofuan and the solution was filtered through Celite to remove insoluble salt. The product was precipitated upon addition of hexane. The green-brown solid was washed with 50 mL of hexane three times and then dried under vacuum to obtain the complex A-1. The yield was 1.3 g (82%).

FTIR (vCO, THF): 2003 m, 1962 vs, 1934 m, 1914 s, 1898 m cm$^{-1}$.

$^1$H NMR (500 MHz, d-THF): 6.54 (t), 6.61 (t), 7.07 (m), 7.21 (m), 7.36 (d), 7.48 (m), 7.58 (m), 7.68 (m), 7.74 (m) ppm.

$^{31}$P{$^1$H} NMR (202.48 MHz, d-THF): 144.2 (s), 21.9 (s) ppm.

Elementary analysis: Calcd for $C_{59}H_{44}Fe_2NO_5P_3S_2$: N, 1.26%; C, 63.51%; H, 3.97%. Anal. Found: N, 1.25%; C, 63.46%; H, 4.37%.

ESI-mass: m/z 577.0 (M−).

Step 3-2

Synthesis of [(μ-bdt-CHCl$_2$)(μ-PPh$_2$)Fe$_2$(CO)$_5$] (complex A-2)

Complex A-1, namely [PPN][(μ-bdt)(μ-PPh$_2$)Fe$_2$(CO)$_5$] (456 mg, 0.41 mmol) was dissolved in 15 mL of a mixed solution of tetrahydrofuan/chloroform (v/v 1/1) and the solution was stirred overnight. The resulting orange-brown solution was filtered through Celite and was concentrated under reduced pressure. An orange solid was appeared upon addition of hexane. The solid was washed by diethyl ether/hexane twice and dried in vacuo to obtain complex A-2. The yield was 81 mg (30%).

FTIR (vCO, THF): 2034 m, 1994 vs, 1962 s, 1942 m cm$^{-1}$.

$^1$H NMR (500 MHz, CDCl$_3$): 6.88 (5), 7.30 (m), 7.59 (m), 7.71 (m), 7.76 (t) ppm.

$^{31}$P{$^1$H} NMR (202.48 MHz, CDCl$_3$): 152.29 (s) ppm.

Elementary analysis: Calcd for $C_{49}H_{34}Cl_4Fe_4O_{10}P_2S_4$: C, 43.60%; H, 2.29%. Anal. Found: C, 43.47%; H, 2.55%.

FAB-mass: m/z 659.8 (M+).

Preparing Example 2

Synthesis of [K-18-crown-6-ether][(μ-pdt)(μ-PPh$_2$)Fe$_2$(CO)$_5$] (complex A-3, which has the structure of formula (II-2))

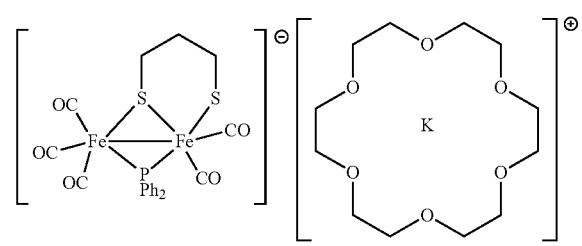

II-2

A diiron dithiolate complex, [K-18-crown-6-ether][(μ-pdt)(μ-PPh$_2$)Fe$_2$(CO)$_5$] (complex A-3), represented by the following formula was synthesized. It is described specifically below.

The diiron dithiolate complex was synthesized according to the method described in Example 1.

First, [(μ-pdt)Fe$_2$(CO)$_6$] (complex 102-2) was prepared according to Step 1 for [(μ-bdt)Fe$_2$(CO)$_6$] (complex 102-1). To a solution of [Fe$_3$(CO)$_{12}$] (0.5 g, 1 mmol, complex 101) in tetrahydrofuan solution (15 mL) was added 1,3-propanedithiol (111 μL, 1.1 mmol). The solution was stirred at 70 K for 0.5 hour to give a red solution. The solution was cooled down and filtered through Celite. The filtrate was dried under vacuo. The red solid was dissolved in hexane (5 mL). The crude product was purified by chromatography on silica gel with dichloromethane/hexane (v/v 1/1) as the eluent. From the red band, the product, [(μ-pdt)Fe$_2$(CO)$_6$] (complex 102-2), was obtained as a red solid (274 mg, 71%).

Next, a 10 mL tetrahydrofuan solution of [(μ-pdt)Fe$_2$(CO)$_6$] (1 g, 2.59 mmol, complex 102-2) was added 0.5 M KPPh$_2$ (5.18 mL, 2.59 mmol) and the solution was stirred for 30 minutes. Then 18-crown-6 ether (686 mg, 2.59 mmol) was added and the reaction mixture was stirred at 298 K for over 3 days. The resulting solution was concentrated to ca. 0.5 mL by reduced pressure. The resulting solution was added ca. 20 mL diethyl ether to give green precipitant. The yield for [K-18-crown-6-ether][(μ-pdt)(μ-PPh$_2$)Fe$_2$(CO)$_5$] (complex A-3) is 1.26 g (53% yield).

FTIR (vCO, THF): 1999 m, 1952 vs, 1926 sh, 1913 s, 1889 w cm$^{-1}$.

$^1$H NMR (500 MHz, d$_8$-THF): 1.54 (m), 1.94 (m), 2.39 (m), 2.75 (m), 3.63 (s), 7.00-7.60 (m) ppm.

$^{31}$P{$^1$H} NMR (202.48 MHz, d$_8$-THF): 140.27 (s) ppm.

Elementary analysis: Calcd for $C_{36}H_{48}Fe_2KO_{12}PS_2$: C, 47.07%; H, 5.27%. Anal. Found: C, 47.23%; H, 5.10%.

ESI-mass: m/z 542.9 (M−).

Preparing Example 3

Synthesis of [K-18-crown-6-ether][(μ-edt)(μ-PPh$_2$)Fe$_2$(CO)$_5$] (complex A-4, which has the structure of formula (II-3))

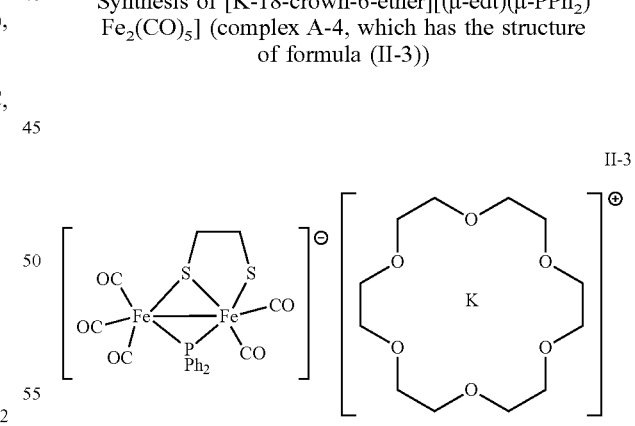

II-3

A diiron dithiolate complex, [K-18-crown-6-ether][(μ-edt)(μ-PPh$_2$)Fe$_2$(CO)$_5$] (complex A-4), represented by the following formula was synthesized. It is described specifically below.

The diiron dithiolate complex was synthesized according to the method described in Example 1.

First, [(μ-edt)Fe$_2$(CO)$_6$] (complex 102-3) was prepared according to Step 1 for [(μ-bdt)Fe$_2$(CO)$_6$] (complex 102-1). To a solution of [Fe$_3$(CO)$_{12}$] (0.5 g, 1 mmol, complex 101) in tetrahydrofuan solution (15 mL) was added 1,2-ethanedithiol (93 μL, 1.1 mmol). The solution was stirred at 343 K for 0.5 hour to give a red solution. The solution was cooled down and filtered through Celite. The filtrate was dried under vacuo. The red solid was dissolved in hexane (5 mL). The crude product was purified by chromatography on silica gel with dichloromethane/hexane (v/v 1/1) as the eluent. From the red band, the product, [(μ-edt)Fe$_2$(CO)$_6$] (complex 102-3), was obtained as a red solid (238 mg, 64%).

Next, a 10 mL tetrahydrofuan solution of [(μ-edt)Fe$_2$(CO)$_6$] (0.5 g, 1.34 mmol, complex 102-3) was added 0.5 M KPPh$_2$ (2.69 mL, 1.34 mmol) and the solution was stirred for 30 minutes. Then 18-crown-6 ether (1.07 g, 4.03 mmol) was added and the reaction mixture was stirred for 30 minutes and stirred at 298 K for over 2 days. The resulting solution was concentrated to ca. 0.5 mL by reduced pressure. The resulting solution was added ca. 20 mL diethyl ether to give green precipitant. The yield for [K-18-crown-6-ether][(μ-edt)(μ-PPh$_2$)Fe$_2$(CO)$_5$] (complex A-4) is 146 mg (13% yield).

FTIR (νCO, THF): 1993 m, 1954 vs, 1917 sh, 1908 s, 1895 w cm$^{-1}$.

$^1$H NMR (500 MHz, d$_8$-THF): 1.9-2.6 (m), 3.63 (s), 7.00-7.70 (m) ppm.

$^{31}$P{$^1$H} NMR (202.48 MHz, d$_8$-THF): 141.19 (s) ppm.

Elementary analysis: Calcd for C$_{31}$H$_{42}$Fe$_2$KO$_{13}$PS$_2$: C, 42.87%; H, 4.87%. Anal. Found: C, 42.99%; H, 4.71%.

ESI-mass: m/z 529.0 (M−).

Preparing Example 4

Synthesis of [PPN][(μ-bdt)(μ-SPh)Fe$_2$(CO)$_5$] (complex A-5, which has the structure of formula (II-4))

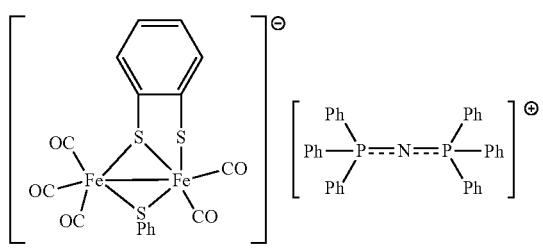

II-4

A diiron dithiolate complex, [PPN][(μ-bdt)(μ-SPh)Fe$_2$(CO)$_5$] (complex A-5), represented by the following formula was synthesized. It is described specifically below.

The diiron dithiolate complex was synthesized according to the method described in Example 1.

A 10 mL tetrahydrofuan solution of [(μ-bdt)Fe$_2$(CO)$_6$] (0.2 g, 0.476 mmol, complex 102-1) was added [PPN]SPh (308 mg, 0.476 mmol) and the solution was stirred for 2 hours. The solution was filtered through Celite and the filtrate was dried under vacuum. The solid was washed with hexane/tetrahydrofuan solution several times to give a dark brown solid. The yield for [PPN][(μ-bdt)(μ-SPh)Fe$_2$(CO)$_5$] (complex A-5) was 79% (391 mg).

FTIR (νCO, THF): 2013 s, 1968 vs, 1942 m, 1928 s, 1906 w cm$^{-1}$.

$^1$H NMR (500 MHz, d$_6$-acetone): 6.61 (t), 6.72 (t), 7.10-7.68 (m) ppm.

Elementary analysis: Calcd for C$_{61}$H$_{43}$Fe$_4$NO$_{11}$P$_2$S$_5$: C, 61.23%; H, 3.78%; N, 1.35%. Anal. Found: C, 61.11%; H, 3.60%; N, 1.39%.

ESI-mass: m/z 500.9 (M−).

Preparing Example 5

Synthesis of [PPN][(μ-bdt)(μ-SEt)Fe$_2$(CO)$_5$] (complex A-6, which has the structure of formula (II-5))

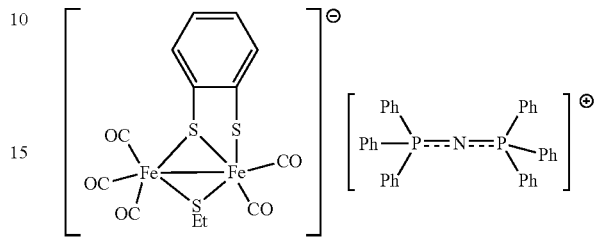

II-5

A diiron dithiolate complex, [PPN][(μ-bdt)(μ-SEt)Fe$_2$(CO)$_5$] (complex A-6), represented by the following formula was synthesized. It is described specifically below.

The diiron dithiolate complex was synthesized according to the method described in Example 1.

A 10 mL tetrahydrofuan solution of [(μ-bdt)Fe$_2$(CO)$_6$] (0.4 g, 0.952 mmol, complex 102-1) was added [PPN]Cl (546.7 mg, 0.952 mmol) and NaSEt (80.2 mg, 0.952 mmol). The solution was stirred for 3 hours. The solution was filtered through Celite and the filtrate was dried under vacuum. The solid was washed with hexane/tetrahydrofuan solution several times to give a brown solid. The yield for [PPN][(μ-bdt)(μ-SEt)Fe$_2$(CO)$_5$] (complex A-6) was 49% (462 mg).

FTIR (νCO, THF): 2009 m, 1964 vs, 1936 m, 1923 s, 1903 w cm$^{-1}$.

$^1$H NMR (500 MHz, d$_6$-acetone): 1.01 (t), 1.83 (m), 6.64 (t), 6.72 (t), 7.31-7.62 (m) ppm.

Elementary analysis: Calcd for C$_{49}$H$_{39}$Fe$_2$NO$_5$P$_2$S$_3$: C, 59.35%; H, 3.96%; N, 1.41%. Anal. Found: C, 59.51%; H, 3.99%; N, 1.45%.

ESI-mass: m/z 452.8 (M−).

Preparing Example 7

Synthesis of [PPN][(μ-bdt)(μ-S$^t$Bu)Fe$_2$(CO)$_5$] (complex A-7, which has the structure of formula (II-6))

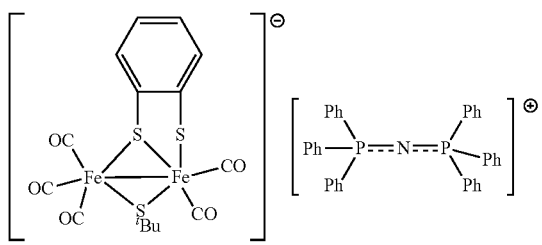

II-6

A diiron dithiolate complex, [PPN][(μ-bdt)(μ-S$^t$Bu)Fe$_2$(CO)$_5$] (complex A-7), represented by the following formula was synthesized. It is described specifically below.

The diiron dithiolate complex was synthesized according to the method described in Example 1.

A 10 mL tetrahydrofuan solution of [(μ-bdt)Fe$_2$(CO)$_6$] (0.4 g, 0.952 mmol, complex 102-1) was added [PPN]Cl (546.7 mg, 0.952 mmol) and NaS$^t$Bu (106.8 mg, 0.952 mmol). The solution was stirred for 3 hours. The solution was filtered through Celite and the filtrate was dried under vacuum. The solid was washed with hexane/tetrahydrofuan solution several times to give a green brown solid. The yield for [PPN][(μ-bdt)(μ-S$^t$Bu)Fe$_2$(CO)$_5$] (complex A-7) was 70% (680 mg).

FTIR (vCO, THF): 2008 m, 1965 vs, 1936 m, 1923 s, 1904 w cm$^{-1}$.

$^1$H NMR (500 MHz, d$_6$-acetone): 1.09 (s), 1.31 (s), 6.61 (m), 7.34-7.87 (m) ppm.

Elementary analysis: Calcd for C$_{51}$H$_{43}$Fe$_2$NO$_5$P$_2$S$_3$: C, 60.07%; H, 4.25%; N, 1.37%. Anal. Found: C, 59.95%; H, 4.19%; N, 1.41%.

ESI-mass: m/z 480.9 (M−).

Preparing Example 8

Synthesis of [(μ-bdt)(μ-PPh$_2$)(μ-H)Fe$_2$(CO)$_5$] (complex A-8, which has the structure of formula (I-3))

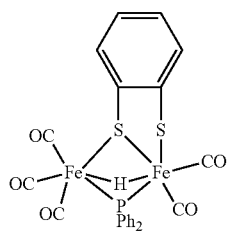

I-3

A diiron dithiolate complex, [(μ-bdt)(μ-PPh$_2$)(μ-H)Fe$_2$(CO)$_5$] (complex A-8), represented by the following formula was synthesized. It is described specifically below.

The diiron dithiolate complex was synthesized according to the method described in Example 1.

A dichlorometahne solution (10 mL) of complex A-1 (357 mg, 0.32 mmol) was treated with HOTf (29 μL, 0.32 mmol). The solution was stirred for 10 min at 298 K. The olive-green solution was filtered and dried in vacuo. Hexane was added to extract the product. The solution was dried under reduced pressure to obtain the olive-green semi-solid. The yield for [QJ-bdt)(μ-PPh$_2$)(μ-H)Fe$_2$(CO)$_5$] (complex A-8) was 166 mg (90%).

FTIR (vCO, THF): 2080 s, 2031 vs, 2013 s, 1984 m cm$^{-1}$.

$^1$H NMR (500 MHz, CD$_2$C$_{12}$): 6.91-7.72 (m), 14.08 (d) ppm.

$^{31}$P{$^1$H} NMR (202.48 MHz, CD$_2$C$_{12}$): 130.9 (s) ppm.

Preparing Example 9

Synthesis of [(μ-Hbdt)(μ-PPh$_2$)(μ-H)Fe$_2$(CO)$_5$][OTf] (complex A-9, which has the structure of formula (II-7))

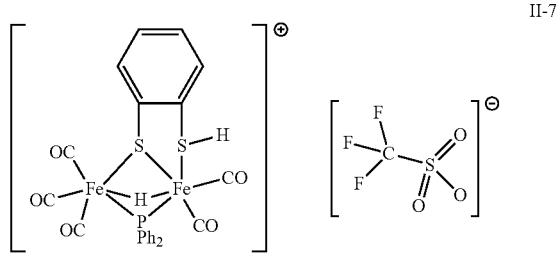

II-7

A diiron dithiolate complex, [(μ-Hbdt)(μ-PPh$_2$)(μ-H)Fe$_2$(CO)$_5$][OTf] (complex A-9), represented by the following formula was synthesized. It is described specifically below.

The diiron dithiolate complex was synthesized according to the method described in Example 1.

To a dichloromethane solution (8 mL) of complex A-1 (446 mg, 0.40 mmol) was added HOTf (180 μL, 2.03 mmol). The solution was stirred for 10 minutes at 298 K, during which time the solution color changed from green-brown, orange yellow and finally orange red. The orange-red solution was filtered and was concentrated under reduced pressure. An orange-red semi-solid was appeared upon addition of hexane. The solid was washed by hexane twice and dried in vacuo. The yield for [(μ-Hbdt)(μ-PPh$_2$)(μ-H)Fe$_2$(CO)$_5$][OTf] was 239 mg (82%).

FTIR (vCO, CH$_2$Cl$_2$): 2101 s, 2059 vs, 2041 s, 2017 m cm$^{-1}$.

FTIR (vSH, KBr): 2469 br cm$^{-1}$.

$^1$H NMR (500 MHz, CD$_2$Cl$_2$): −15.62 (d), 6.27 (s), 7.24-7.80 (m) ppm.

$^{31}$P{$^1$H} NMR (202.48 MHz, CD$_2$Cl$_2$): 145.8 (s) ppm.

Elementary analysis: Calcd for C$_{255}$H$_{19}$C$_1$F$_6$Fe$_2$O$_{11.5}$PS$_4$: C, 32.94%; H, 2.06%. Anal. Found: C, 33.02%; H, 2.48%.

ESI-mass: m/z 579.0 (M+).

Preparing Example 10

Synthesis of [(μ-bdt)(μ-PPh$_2$)Fe$_2$(CO)$_5$]$^-$ (complex 2, which has the structure of formula (I-1))

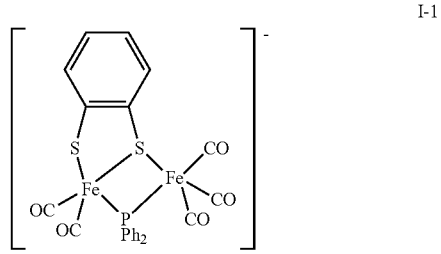

I-1

A diiron dithiolate complex, [(μ-bdt)(μ-PPh$_2$)Fe$_2$(CO)$_5$]$^-$ (complex 2), represented by the following formula was synthesized. It is described specifically below.

The diiron dithiolate complex was synthesized according to the method described in Example 1.

The iron-sulfur complex used as a catalyst was [(μ-bdt)(μ-PPh$_2$)Fe$_2$(CO)$_5$]$^-$ (complex 2, wherein bdt means 1,2-benzenedithiolate), which was generated from the reaction of [(μ-bdt)Fe$_2$(CO)$_6$] (complex 102-1) with [PPh$_2$]$^-$, a general procedure for preparation of complex A-1. Complex 2 has a dark green-brown color. The anionic core of complex 2 is similar to that of complex A. Some degree of structural distortion occurs with different counter ions. Therefore, formula I-1 can be considered as a general description for complexes 2, A-1 and other related derivatives. In addition to complex A-1, a series of complexes 2 with various cations are prepared for comparison.

The complex was characterized using spectroscopy and X-ray crystallography. In the structure, two Fe centers are bridged by PPh$_2$ and one of the thiolate ends of the bdt ligand. The other thiolate site is swung away from the Fe center. Both of the two bridging groups PPh$_2$ and bdt are asymmetrically coordinated to the metal sites. For instance, the Fe—Fe bond distance (2.6163(14) Å) in complex A-1 is comparable to those of the DFT optimized structures: 2.56 Å for [(μ-pdt)Fe$_2$(CO)$_6$] (pdt=1,3-propanedithiolate) and 2.653 Å for [(t-pdt)Fe$_2$(CN)3(CO)$_3$] where a Fe moiety is rotated by 60° to generate a distorted structure with a semi-bridging CO group.

[Li(THF)4][(μ-bdt)(μ-PPh$_2$)Fe$_2$(CO)$_5$] (complex 2-1)

The yield: 81%.

FTIR (vCO, THF): 2003 m, 1962 vs, 1934 m, 1915 s, 1898 m cm$^{-1}$.

$^1$H NMR (500 MHz, d$_8$-THF): 1.73 (m), 3.56 (m), 6.55 (t), 6.64 (t), 7.06-7.68 (m) ppm.

$^{31}$P{$^1$H} NMR (202.48 MHz, d$_8$-THF): 144.57 (s) ppm.

Elementary analysis: Calcd for C$_{33}$H$_{34}$Fe$_2$LiO$_{7.5}$PS$_2$: C, 51.85%; H, 4.48%. Anal. Found: C, 51.50%; H, 4.88%.

ESI-mass: m/z 577.0 (M–).

[TBA][(μ-bdt)(μ-PPh$_2$)Fe$_2$(CO)$_5$] (complex 2-2)

The yield: 78%.

FTIR (vCO, THF): 2005 m, 1961 vs, 1936 m, 1916 s, 1896 m cm$^{-1}$.

$^1$H NMR (500 MHz, d$_8$-THF): 0.97 (t), 1.36 (m), 1.60 (m), 3.15 (m), 6.63 (t), 6.72 (t), 7.11-7.72 (m) ppm.

$^{31}$P{$^1$H} NMR (202.48 MHz, d$_8$-THF): 144.7 (s) ppm.

Elementary analysis: Calcd for C$_{39}$H$_{50}$Fe$_2$NO$_5$PS$_2$: C, 57.15%; H, 6.15%; N, 1.71%. Anal. Found: C, 57.040%; H, 6.12%; N, 1.92%.

ESI-mass: m/z 576.9 (M–).

Testing Examples

Testing Example 1

Catalysis of Acids with Strong Strength

1. Production of Hydrogen from Hydrochloric Acid by Complex A-1

Figure 3:
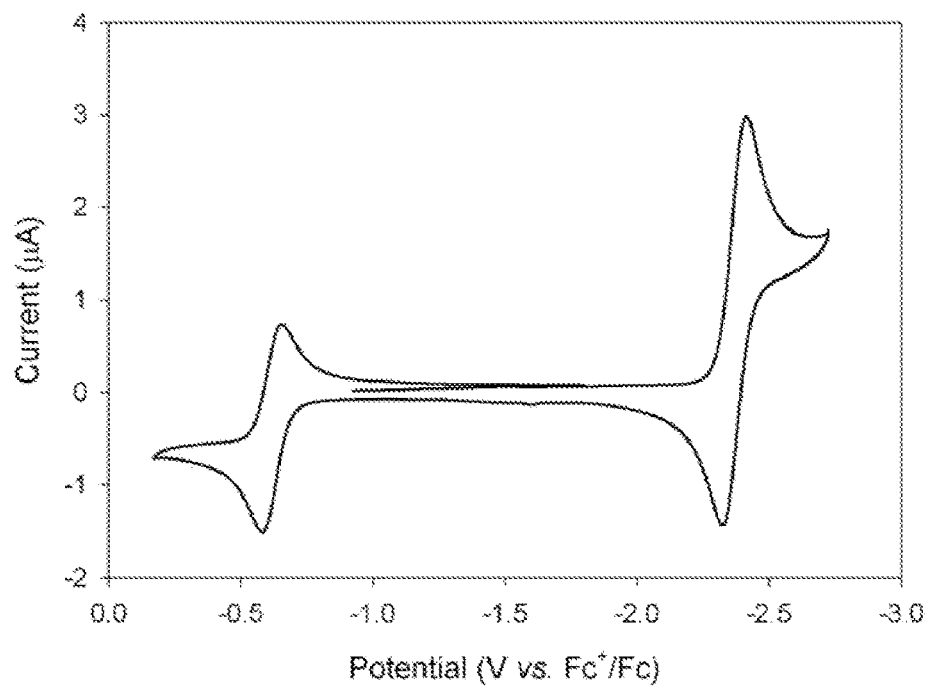
FIG. 3 shows a cyclic voltammogram of complex A-1 in tetrahydrofuran solution (1 mM, scan rate=100 mV/s, 0.1 M n-Bu$_4$NPF$_6$, 1 mm vitreous carbon electrode, 295 K) under N$_2$. $E_{1/2}^{ox}$=−0.62 V and $E_{1/2}^{red}$=−2.37 V, in Testing Example 1.
Figure 4:
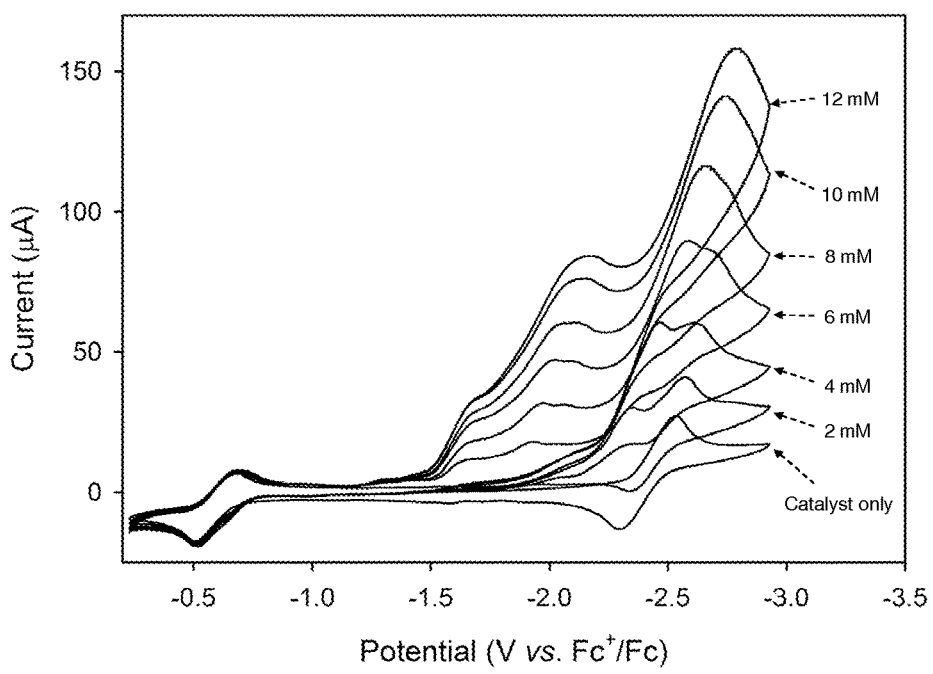
FIG. 4 shows cyclic voltammograms of complex A-1 (blank), with hydrochloric acid 2, 4, 6, 8, 10 and 12 mM in tetrahydrofuran solution (1 mM, scan rate=100 mV/s, 0.1 M n-Bu$_4$NPF$_6$, 3 mm vitreous carbon electrode, 291 K) under N$_2$, in Testing Example 1.

The diiron dithiolate complex (complex A-1) produced in Preparing Example 1 was dissolved in tetrahydrofuran to give a 0.5 mM solution. The solution was transferred to a 3-electrode electrochemical cell. In the absence of acid, cyclic voltammograms of complex A-1 revealed a reversible one-electron oxidation event at −0.62 V and a reversible reduction event at −2.37 V, which consists of two overlapping one-electron processes, shown in FIG. 3. The voltammetry was recorded in tetrahydrofuran solution with 1 mM of A-1 at 295 K under N$_2$. The solution contained 0.1 M n-Bu$_4$NPF$_6$ electrolyte. A scan rate of 100 mV/s and 1 mm vitreous carbon electrode were applied. All electrochemical processes are diffusion-controlled. To this solution, hydrochloric acid was added by syringe. New waves were observed, shown in FIG. 4. The peak current of the wave shows linear increase with sequential increments of acids added, suggesting a catalytic response of hydrogen production. FIG. 4 displays that the catalytic waves grow in intensity as addition of acid at 291 K. Cyclic voltammograms of complex A-1 (1 mM) in the presence of hydrochloric acid (pK$_a$=−7.0 in H$_2$O) 2, 4, 6, 8, 10 and 12 mM in tetrahydrofuran solution were recorded at scan rate of 100 mV/s with 3 mm vitreous carbon electrode and 0.1 M n-Bu$_4$NPF$_6$ under N$_2$. The gas product was detected by GC, confirming the gas content being solely molecular hydrogen.

2. Electrocatalytic Mechanism of Production of Hydrogen from Acids with Strong Strength by Complex A-1

A catalytic mechanism of hydrogen production involving acids with strong strength by the diiron dithiolate complex (complex A-1) produced in Preparing Example 1 is shown in the Scheme 3. As shown in the Scheme 3, the diiron dithiolate complex reacts with protons to generate a Fe-hydride complex, followed by formation of a Fe-hydride-SH complex where second protonation occurs onto the sulfur site when acid is added into the solution containing the complex (complex A-1). Upon electrolysis, hydrogen gas is generated with formation of the Fe-hydride complex. This reaction is denoted as eq. 1 in Scheme 3. It is a hydrogen-production process. The second portion of hydrogen gas is generated, which regenerates the parent complex (complex A-1) to complete the catalytic cycle. This reaction is denoted as eq. 2 in Scheme 3. It is also a hydrogen-production process. In the whole catalytic cycle, there are two hydrogen-production routes.

Scheme 3

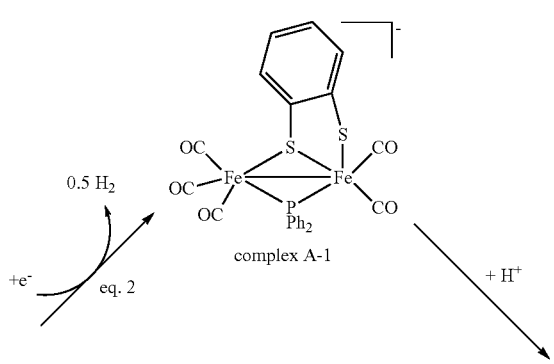

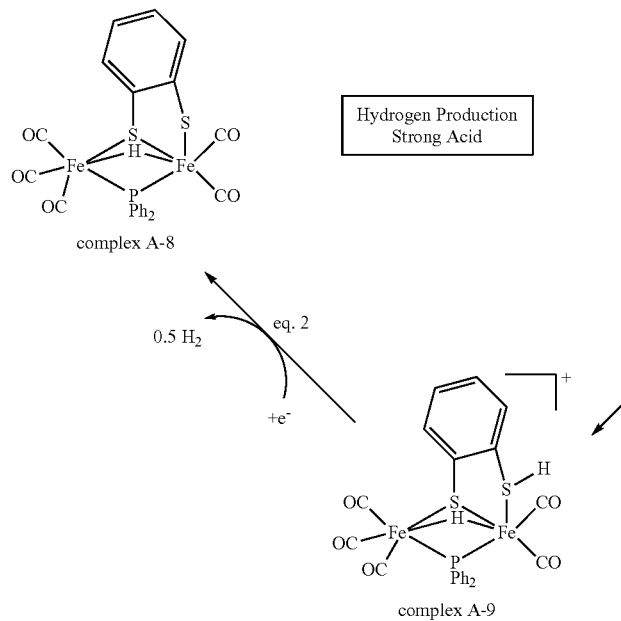

The Fe-hydride complex is denoted as complex A-8 which has the structure of formula (I-3).

I-3

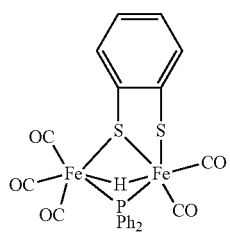

As shown in complex A-8, there is a hydride bridging between two Fe centers, resulted from protonation onto the Fe—Fe vector of complex A-1.

Figure 5:
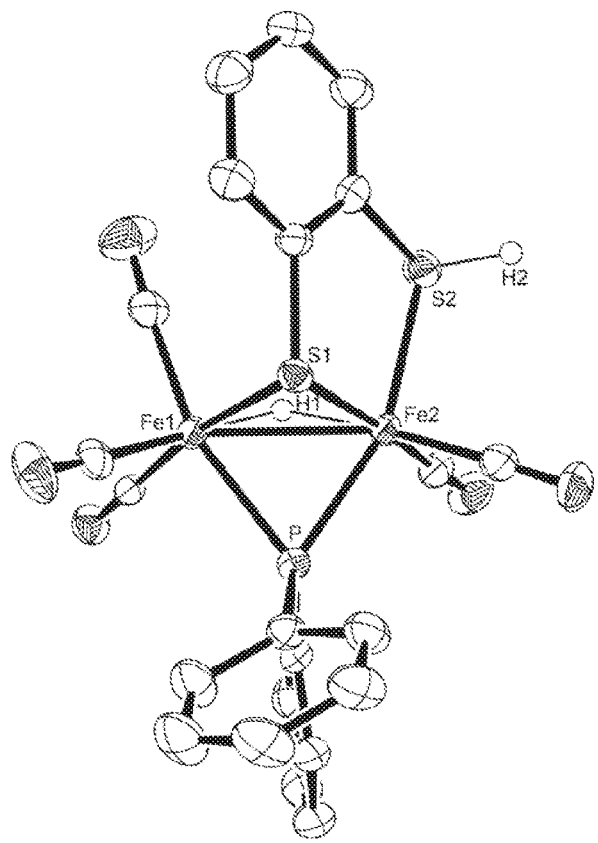
FIG. 5 shows the molecular structure for the cationic part of complex A-9 whose anionic counterpart is omitted for clarity.

The Fe-hydride-SH complex is denoted as complex A-9, which has the structure of formula (II-7) One of the species is displayed as an example (complex A-9) and shown in FIG. 5, where the molecular structure for the cationic part of complex A-9 is shown, while its anionic counterpart is omitted for clarity.

II-7

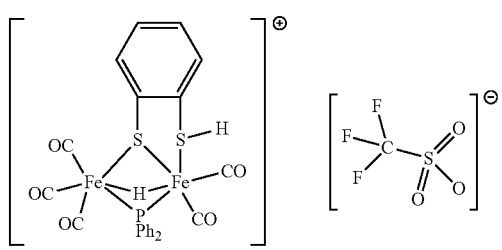

The important bond distances are listed in the corresponding table. It occurs from the reaction of complex A-8 with acid. The sulfur site of complex A-8 is protonated to generate a thiol group coordinated to the Fe center.

Testing Example 2

Catalysis of Acids with Medium Strength

1. Production of Hydrogen from Anilinium Acid by Complex A-1

Figure 6:
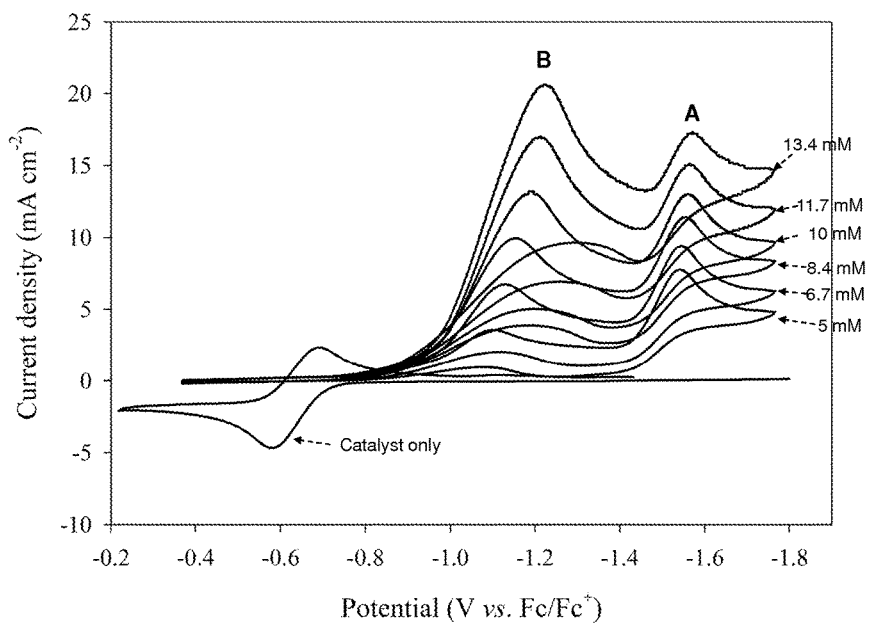
FIG. 6 shows cyclic voltammograms of complex A-1 (blank), with anilinium acid 5, 6.7, 8.4, 10, 11.7 and 13.4 mM in dichloromethane solution (2.44 mM, scan rate=100 mV/s, 0.1 M n-Bu$_4$NBArF$_{24}$ (BArF$_{24}$=B(3,5-C$_6$H$_3$(CF$_3$)$_2$)$_4^-$), 3 mm vitreous carbon electrode, 295 K) under N$_2$, in Testing Example 2.
Figure 7:
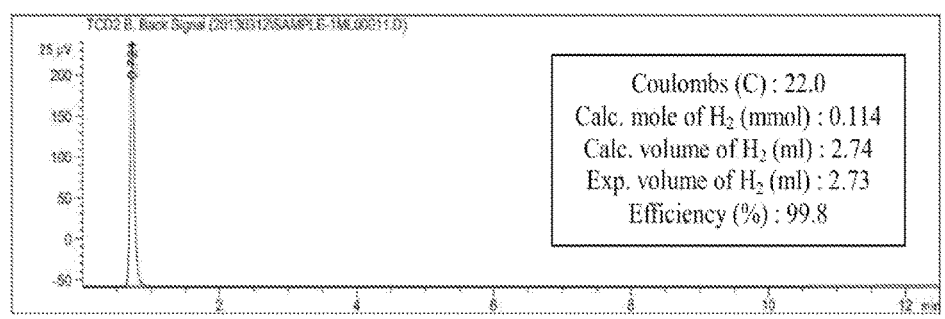
FIG. 7 shows the result of the GC analysis of the gaseous content from the controlled-potential electrolysis. The analysis was performed on an Agilent 7890 GC equipped with a thermal conductivity detector (TCD) and fitted with a Restek ShinCarbon ST column (100/120 mesh, 2 m, 1/16 in. OD, 1.0 mm ID). Carrier gas was nitrogen, in Testing Example 2.

The diiron dithiolate complex (complex A-1) produced in Example 1 was dissolved in dichloromethane to give a 0.5 mM solution. The solution was transferred to a 3-electrode electrochemical cell. In the absence of acid, cyclic voltammograms of complex A-1 revealed a reversible one-electron oxidation event and a reversible reduction event which consists of two overlapping one-electron processes. All electrochemical processes are diffusion-controlled. To this solution, anilinium acid was added by syringe. Two new waves (wave A and B) were observed. FIG. 6 shows cyclic voltammograms of complex A-1 (blank), with anilinium acid ($pK_a$=10.7 in acetonitrile) 5, 6.7, 8.4, 10, 11.7 and 13.4 mM in dichloromethane solution (2.44 mM, scan rate=100 mV/s, 0.1 M n-Bu$_4$NBArF$_{24}$ (BArF$_{24}$=B(3,5-C$_6$H$_3$(CF$_3$)2)$_4^-$), 3 mm vitreous carbon electrode, 295 K) under N$_2$. The electrochemical results display two new electrochemical waves: one new wave (wave A) is located at the more negative potential and the other wave (wave B) is at the more positive potential. For wave B, the peak current of this wave shows linear increase with sequential increments of acids added, suggesting a catalytic response of hydrogen production. The gas product was detected by GC, confirming the gas content being solely molecular hydrogen. The Faradaic efficiency is determined to be over 99%, confirmed by gas chromatography (GC) analysis of gas samples in the head space (FIG. 7).

Figure 8:
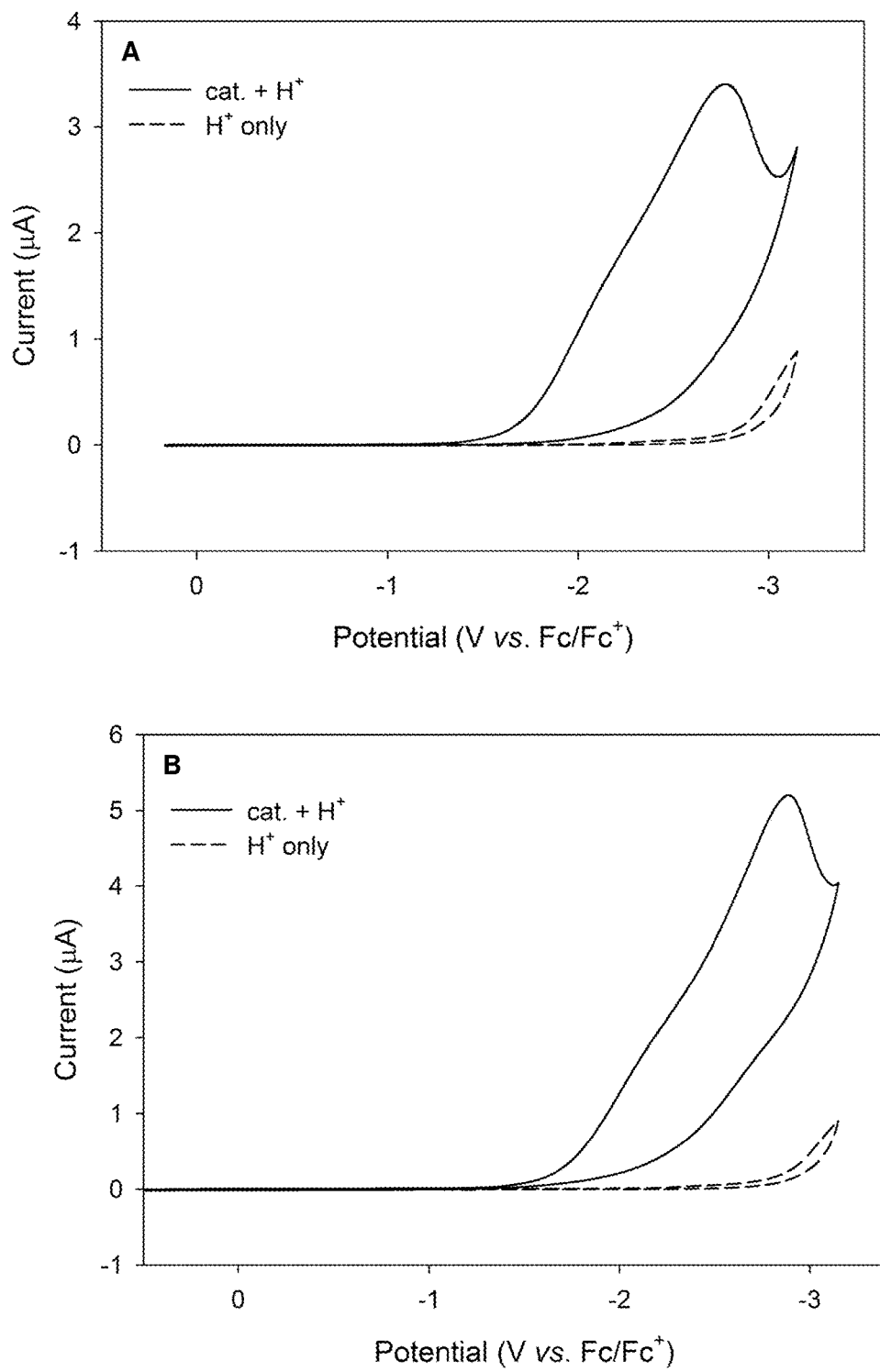
FIG. 8 shows cyclic voltammograms of anilinium acid with and without complex A-1 at various scan rates ([H$^+$] 200 mM, 33 μm carbon fiber electrode, with iR compensation). Scan rate=(A) 16, (B) 25 V/s. The dashed lines represent the acid-only responds. The solid lines represent the catalytic responds involving complex A-1 (0.5 mM), showing that the presence of complex A-1 decreases the working potential by 1.4 V, in Testing Example 2.
Figure 9:
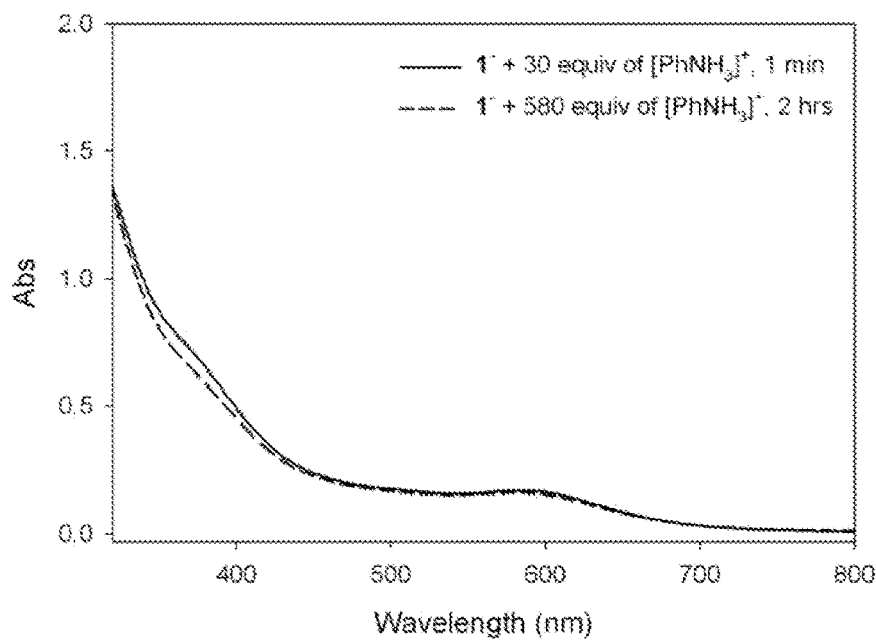
FIG. 9 shows UV-vis spectra of dichloromethane solution containing complex A-1 and anilinium acid. A black line displays the spectrum recorded with 30 equiv of acid after mixing for 1 minute. Additional 550 equiv of acid was added to the same solution and it was stirred for 2 hours at ambient temperature. The resultant spectrum is shown in a dashed line. No visible change was observed, in Testing Example 2.

FIG. 8 reveals a potential difference of the catalysis between the reaction with and without complex A-1 (0.5 mM). The presence of the catalyst (complex A-1) decreases the working potential. In FIGS. 8-A and 8-B, the voltammograms recorded at a scan rate of 16 V s$^{-1}$ and 25 V s$^{-1}$, respectively in the presence of 400 equiv of acid are reported. As shown in the figure, the onset potential of the catalytic wave of acid (without complex A-1, dashed line; with A-1, solid line) is shifted to more positive values by 1.4 V. Stability of complex A-1 for catalysis is shown in FIG. 9. The diiron dithiolate complex (complex A-1) produced in Example 1 was dissolved to give a 0.5 mM solution. UV-vis spectra of the dichloromethane solution containing complex A-1 and 30 equiv. of acid after mixing for 1 minute (black line) and the same solution with additional 550 equiv. of acid after stirring for 2 hours (dashed line) do not reveal any visible spectral change.

2. Acid Concentration Dependence of Production of Hydrogen from Anilinium Acid by Complex A-1

Figure 10:
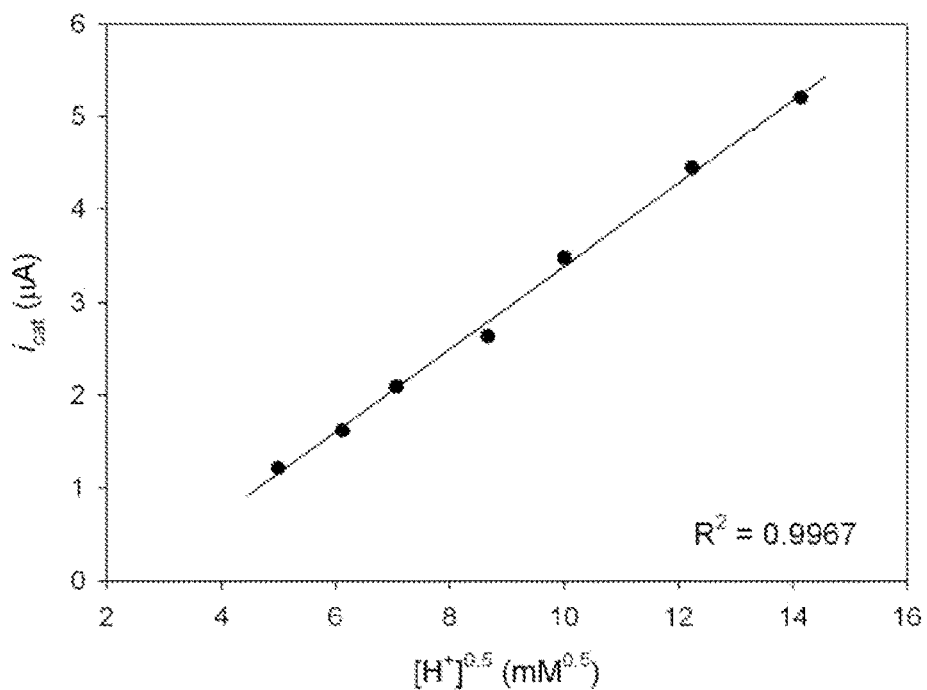
FIG. 10 shows a linear dependence of the catalytic peak current on the square root of acid concentration (25, 37.5, 50, 75, 100, 150, 200 mM), indicating first order with respective to acid for formation of H$_2$. [A-1] 0.5 mM, 33 μm carbon fiber electrode with iR compensation, scan rate=25 V s$^{-1}$, dichloromethane solution, 297 K, in Testing Example 2.

The diiron dithiolate complex (complex A-1) produced in Example 1 was dissolved in dichloromethane to give a 0.5 mM solution. The solution was transferred to a 3-electrode electrochemical cell. The electrolytic hydrogen production was conducted with increments of acid concentration. Linear dependence of the catalytic peak current on the square root of concentrations of acid indicates that the catalytic rate is first order in the concentration of acid, shown in FIG. 10. FIG. 10 displayed the linear relationship between the catalytic peak current and the square root of acid concentration (25, 37.5, 50, 75, 100, 150 and 200 mM), recorded with scan rate of 25 V s$^{-1}$ at 297 K and catalyst concentration of 0.5 mM. As the amount of acids was increased, the catalytic peak current was enhanced and CVs in the catalytic region became shaky in company with vigorous formation of observable gas bubbles. It prevents accurate peak measurements of the catalytic currents when the molar ratio of acid concentration is larger than 600 equiv. It is assumed that faster catalysis could be achieved but evidences fall to be obtained due to experimental restrictions.

3. Scan Rate Dependence of Production of Hydrogen from Anilinium Acid by Complex A-1

Figure 11:
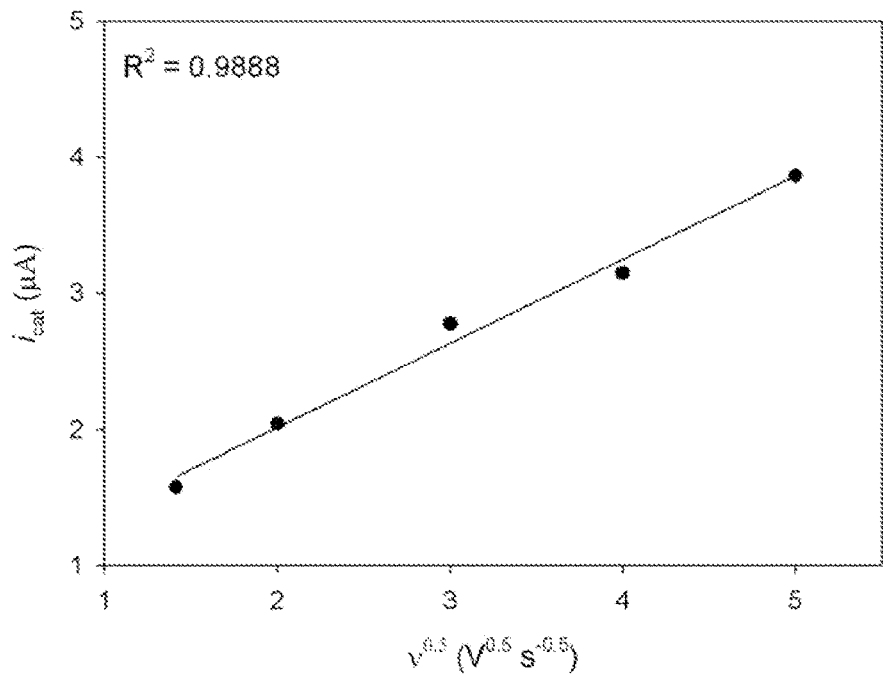
FIG. 11 show a linear dependence of the catalytic peak current on the square root of scan rate (2, 4, 9, 16, 25 V s$^{-1}$) is obtained for acid concentration of 100 mM. [A-1] 0.5 mM, 33 μm carbon fiber electrode with iR compensation, dichloromethane solution, 298 K, in Testing Example 2.
Figure 12:
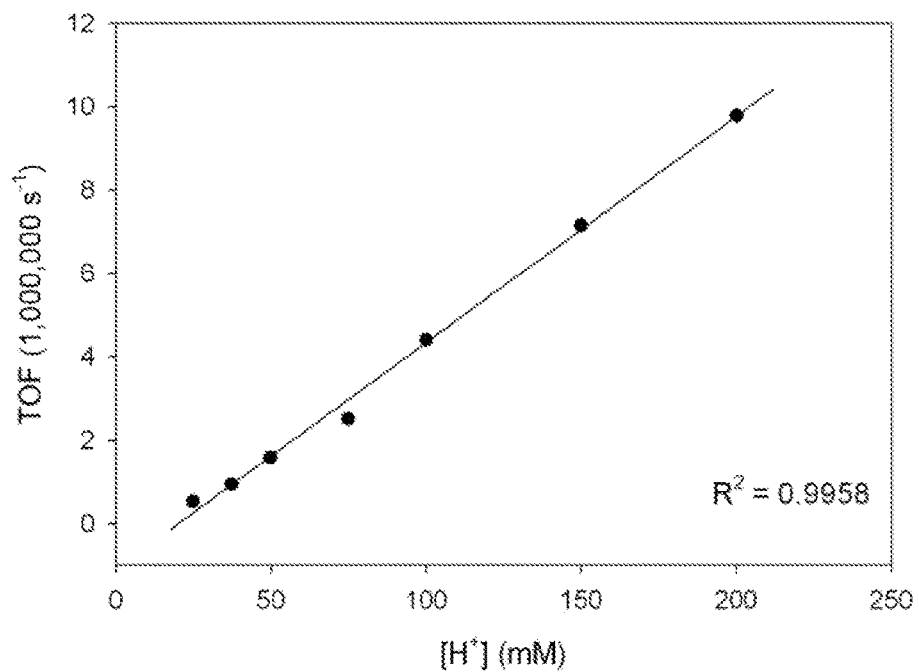
FIG. 12 shows a linear dependence of TOF on acid concentration (25, 37.5, 50, 75, 100, 150, 200 mM). The slope obtained from the linear fit represents the second order rate constant for formation of H$_2$. [A-1] 0.5 mM, 33 μm carbon fiber electrode with iR compensation, scan rate=25 V s$^{-1}$, dichloromethane solution, 297 K, in Testing Example 2.
Figure 13:
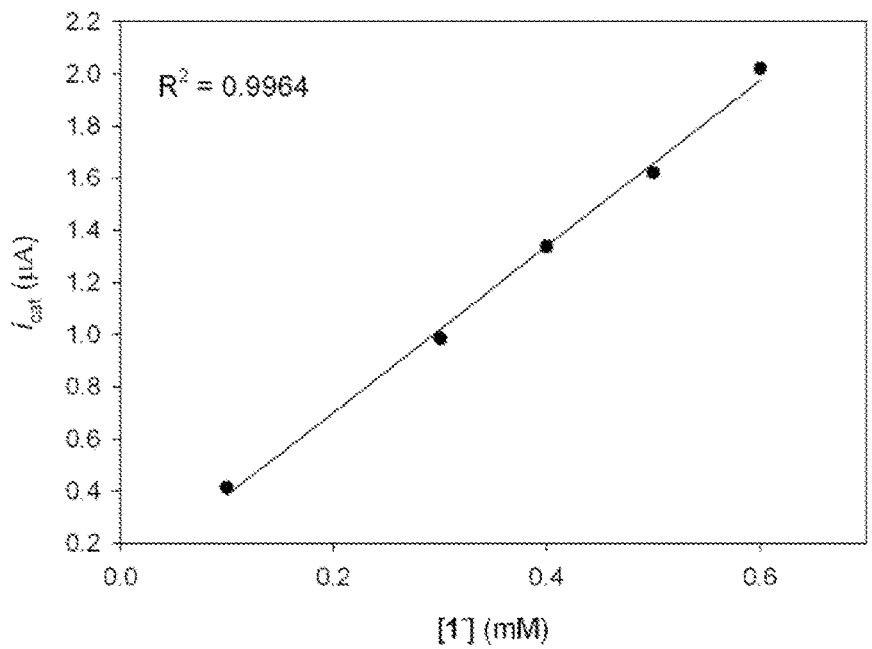
FIG. 13 shows a linear dependence of the catalytic peak current on catalyst concentration (0.1, 0.3, 0.4, 0.5, 0.6 mM), indicating first order with respect to catalyst for formation of H$_2$. [PhNH$_3^+$] 200 mM, 33 μm carbon fiber electrode with iR compensation, scan rate=25 V s$^{-1}$, dichloromethane solution, 297 K, in Testing Example 2.
Figure 14:
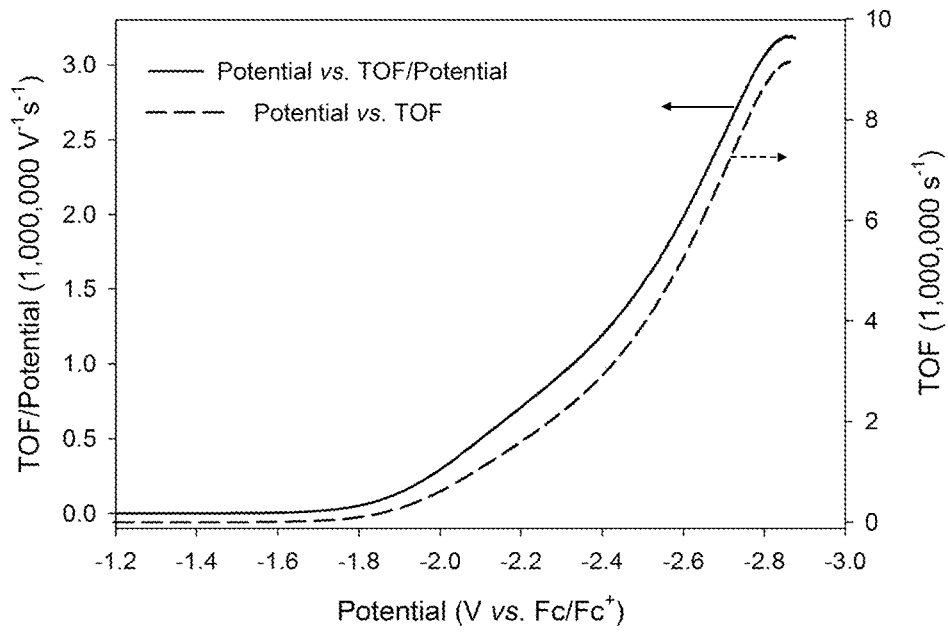
FIG. 14 shows dependence of TOF (dashed line) and TOF per applied voltage (TOF/V$_{app}$, black line) on the working potential. [A-1] 0.5 mM, [PhNH$_3^+$] 200 mM, scan rate of 25 V s$^{-1}$, 33 μm carbon fiber electrode with iR compensation, dichloromethane solution, 297 K, in Testing Example 2.

The diiron dithiolate complex (complex A-1) produced in Example 1 was dissolved in dichloromethane to give a 0.5 mM solution. The solution was transferred to a 3-electrode electrochemical cell. The electrolytic hydrogen production was conducted with increments of acid concentration. Linear dependence of the catalytic peak current on the square root of scan rate of electrochemical processes is observed, shown FIG. 11. FIG. 11 displayed the linear relationship between the catalytic peak current and the square root of scan rate (2, 4, 9, 16, 25 V s$^{-1}$), recorded with acid concentration of 100 mM at 298 K. As scan rate was increased, the catalytic peak current was enhanced and CVs in the catalytic region became shaky in company with vigorous formation of observable gas bubbles. It prevents accurate peak measurements of the catalytic currents when scan rate is greater than 30 V s$^{-1}$. It is assumed that faster catalysis could be achieved but evidences fall to be obtained due to experimental restrictions. The maximum value of TOF for complex A-1 prepared according to Example 1 is calculated to be 9.16×10$^6$ s$^{-1}$. FIG. 12 displays that the TOF value linearly increases with the acid concentration (25, 37.5, 50, 75, 100, 150, 200 mM) under conditions of 0.5 mM of complex A-1, scan rate=25 V s$^{-1}$ and 297 K. The current density for the maximum TOF is 571 mA/cm$^2$. The catalysis is homogeneous in origin and is solely contributed by complex A-1, shown in FIG. 13. FIG. 13 displays a linear dependence of the catalytic peak current on catalyst concentration (0.1, 0.3, 0.4, 0.5, 0.6 mM). The data was recorded at acid concentration of 200 mM, scan rate of 25 V s$^{-1}$ at 297 K. A TOF/V$_{app}$ value (TOF per applied voltage) of 3.2×10$^6$ s$^{-1}$ V$^{-1}$ in term of energy efficiency is obtained. FIG. 14 displays both TOF (dashed line) and TOF/V$_{app}$ (solid line) values with various applied potentials. The results are obtained from the following conditions: [A-1] 0.5 mM, [H$^+$] 200 mM, scan rate of 25 V s$^{-1}$, 33 μm carbon fiber electrode with iR compensation, dichloromethane solution, 297 K.

4. Examination of Catalyst Deposition onto the Surface of the Working Electrode

Figure 15:
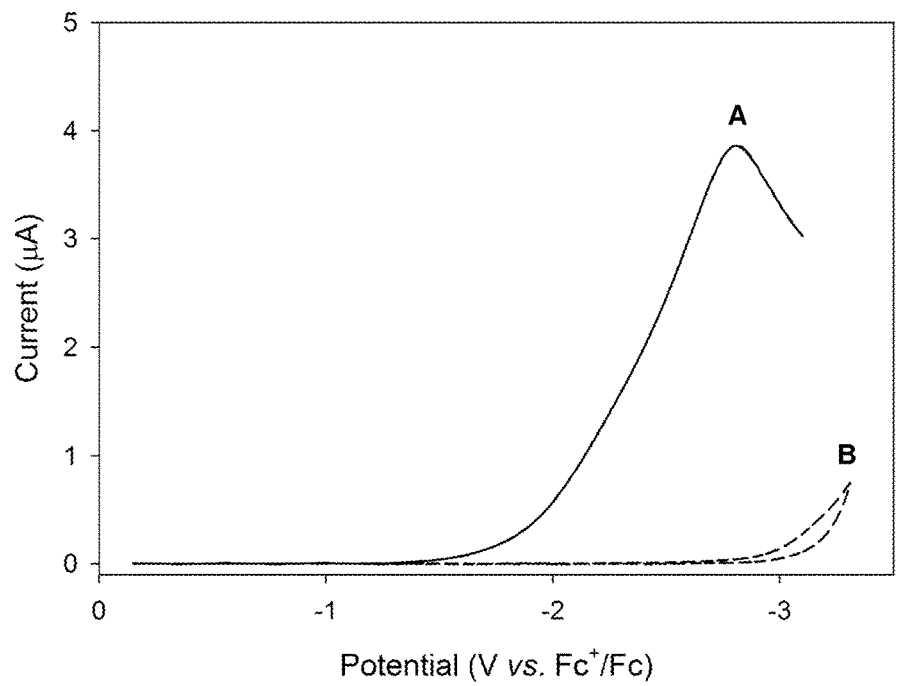
FIG. 15 shows Linear sweep voltammogram of solution A (solid line, [A-1] 0.5 mM, [PhNH$_{3+}$]$_{100}$ mM, scan rate=25 V s$^{-1}$, freshly polished 33 μm of solution A (solid line, iR compensation, 294 K) and cyclic voltammogram of solution B (dashed line, [PhNH$_{3+}$]$_{100}$ mM, scan rate=25 V s$^{-1}$, 33 μm carbon fiber electrode with iR compensation after used for the measurement of solution A, 294 K), in Testing Example 2.

The diiron dithiolate complex (complex A-1) produced in Example 1 was dissolved in dichloromethane to give a 0.5 mM solution. Two electrochemical cells were prepared. The catalyst solution was transferred to cell A. In cell B, no catalyst was added. The same amount of anilinium acid (100 mM) was added into both cells. The voltammograms corrected with iR compensation were recorded with scan rate=25 V s$^{-1}$ at 294 K under N$_2$. A 33 μm carbon fiber electrode was polished to 1.0 and 0.05 μm alumina on micropolishing cloth prior to electrochemical measurements. The first linear sweep voltammogram was recorded in solution A of cell A. The electrode was removed from solution A and rinsed with tetrahydrofuran. The electrode was dipped into solution B for measurement of the follow-up cyclic voltammogram starting from −1.5 V. FIG. 15 displays both voltammetric curves from solution A (solid line) and B (dashed line). No catalytic event was observed for solution B, indicating that the high current catalytic responds observed at high acid concentrations are resulted from the soluble diiron dithiolate complex (complex A-1) in solution (i.e. solution A).

Testing Example 3

Catalysis of Acids with Weak Strength and in Aqueous Solution

1. Production of Hydrogen from Acetic Acid by Complex A-1

Figure 16:
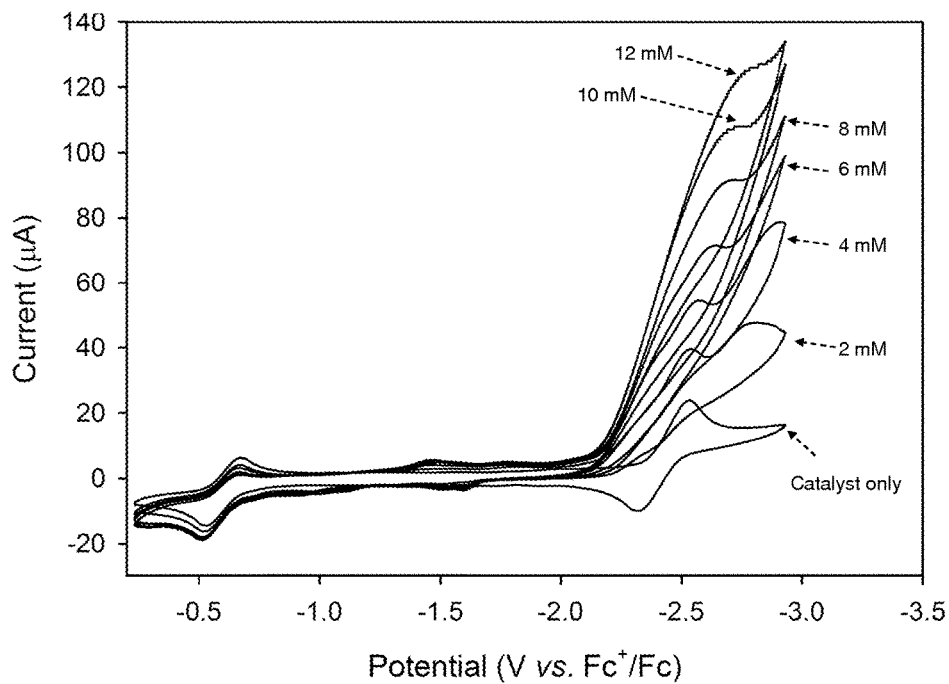
FIG. 16 shows cyclic voltammograms of complex A-1 (blank), with acetic acid 2, 4, 6, 8, 10 and 12 mM in tetrahydrofuan solution (3 mM, scan rate=100 mV/s, 0.1 M n-Bu$_4$NPF$_6$, 1 mm vitreous carbon electrode, 293 K) under N$_2$, in Testing Example 3.

The diiron dithiolate complex (complex A-1) produced in Example 1 was dissolved in tetrahydrofuran to give a 0.5 mM solution. The solution was transferred to a 3-electrode electrochemical cell. In the absence of acid, cyclic voltammograms of complex A-1 revealed a reversible one-electron oxidation event and a reversible reduction event which consists of two overlapping one-electron processes. All electrochemical processes are diffusion-controlled. To this solution, acetic acid (pK$_a$=22.3 in acetonitrile) was added by syringe. A catalytic wave was observed. The peak current of this wave shows linear increase with sequential increments of acids added in accompany with evolution of hydrogen gas. FIG. 16 displays that the catalytic wave grows in intensity as addition of acid (2, 4, 6, 8, 10, and 12 mM) at 293 K with scan rate=100 mV/s, 0.1 M n-Bu$_4$NPF$_6$, 3 mm vitreous carbon electrode. The gas product was detected by GC, confirming the gas content being solely molecular hydrogen. Faraday yield is estimated to exceed 97%.

Figure 17:
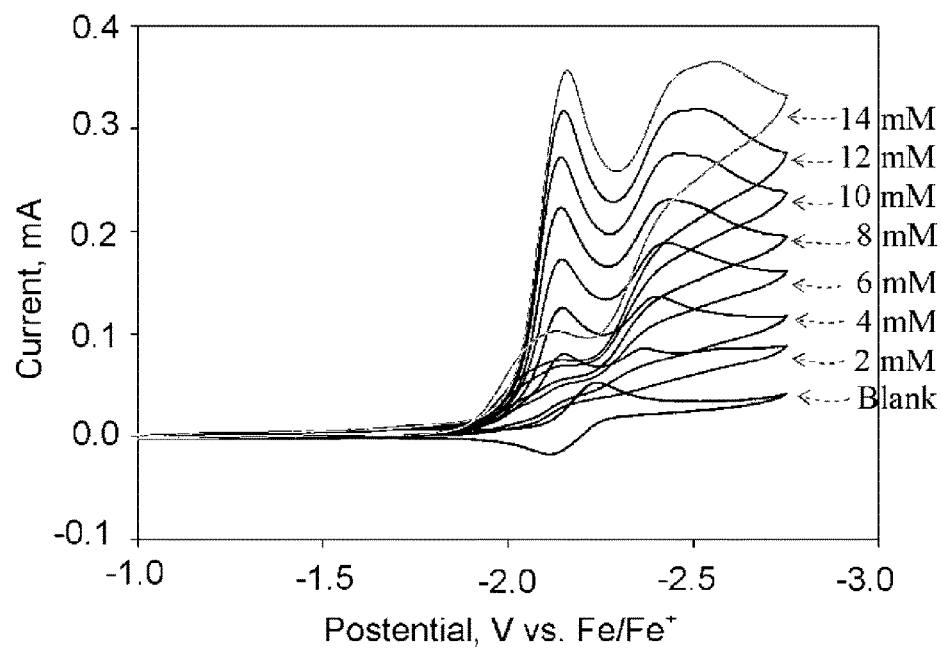
FIG. 17 shows cyclic voltammograms of A-1 (blank), with acetic acid 2, 4, 6, 8, 10, 12 and 14 mM in acetonitrile solution (1 mM, scan rate=100 mV/s, 0.1 M n-Bu$_4$NPF$_6$, 1 mm vitreous carbon electrode, 296 K) under N$_2$, in Testing Example 3.
Figure 18:
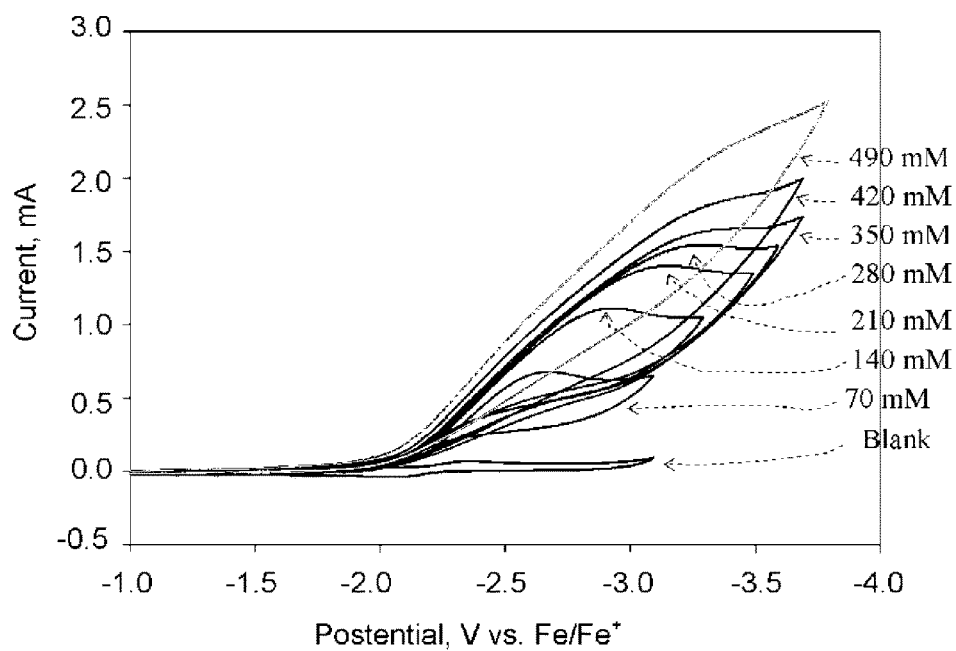
FIG. 18 shows cyclic voltammograms of A-1 (blank), with acetic acid 70, 140, 210, 280, 350, 420 and 490 mM in acetonitrile solution (1 mM, scan rate=29.4 V/s, 0.1 M n-Bu$_4$NPF$_6$, 1 mm vitreous carbon electrode, 292 K) under N$_2$, in Testing Example 3.
Figure 19:
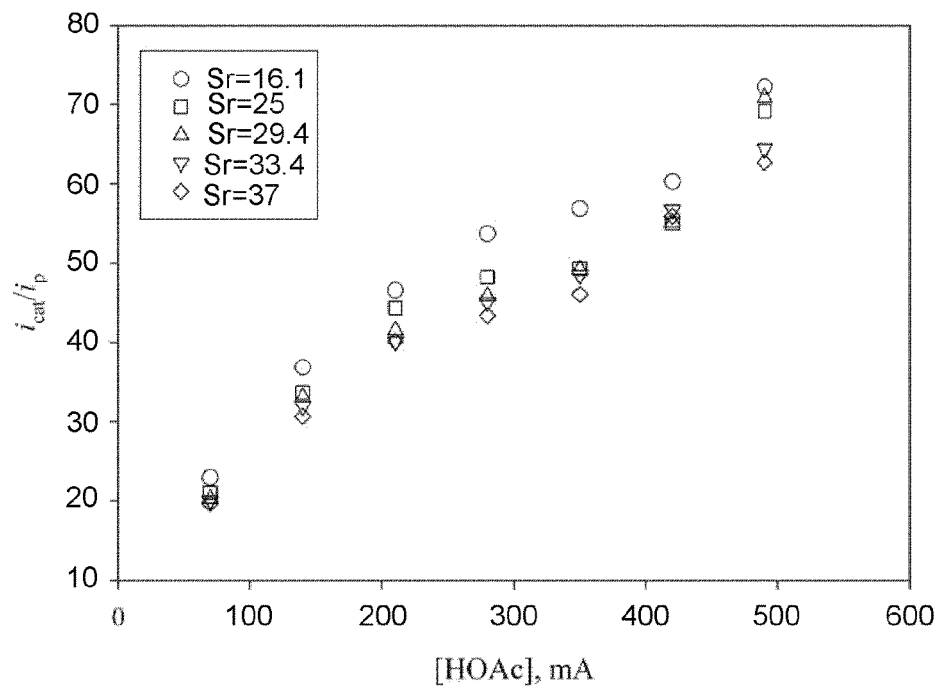
FIG. 19 shows the dependence of $i_{cat}/i_p$ on the concentration of acetic acid (70, 140, 210, 280, 350, 420 and 490 mM) under different scan rates (16.1, 25, 29.4, 33.4, 37 V s$^{-1}$), in Testing Example 3.

The electrochemistry of A-1 was also investigated in acetonitrile solution, using acetic acid as proton sources. As shown in FIG. 17, two reductions were recorded at −2.15 V and −2.37 V vs. the ferrocene/ferrocenium couple under acidic condition (2, 4, 6, 8, 10, 12, 14 mM) in acetonitrile solution. The results were recorded at scan rate of 100 mV/s, 0.1 M n-Bu$_4$NPF$_6$, 1 mm vitreous carbon electrode at 296 K. The first reduction process reveals a catalytic event in which its current linearly increases with the increment of acid concentration. FIG. 18 shows cyclic voltammograms of A-1 (blank), with acetic acid 70, 140, 210, 280, 350, 420 and 490 mM in acetonitrile solution (1 mM, scan rate=29.4 V/s, 0.1 M n-Bu$_4$NPF$_6$, 1 mm vitreous carbon electrode, 292 K) under N$_2$. The dependence of $i_{cat}/i_p$ on the concentration of acetic acid (70, 140, 210, 280, 350, 420 and 490 mM) under different scan rates (16.1, 25, 29.4, 33.4, 37 V s$^{-1}$) is displayed in FIG. 19. As shown in FIGS. 18 and 19, when the scan rate was 29 V s$^{-1}$ and the acid concentration was 490 mM, the catalytic peak current was 71 times the acid-free peak current, which corresponds to TOF of 291, 000 s$^{-1}$. The gas content was confirmed to molecular hydrogen by GC. The Faraday yield is estimated to exceed 95%. The second new wave located at the more negative potential is non-catalytic.

2. Production of Hydrogen from Aqueous Methanol Solution by Complex A-1

Figure 20:
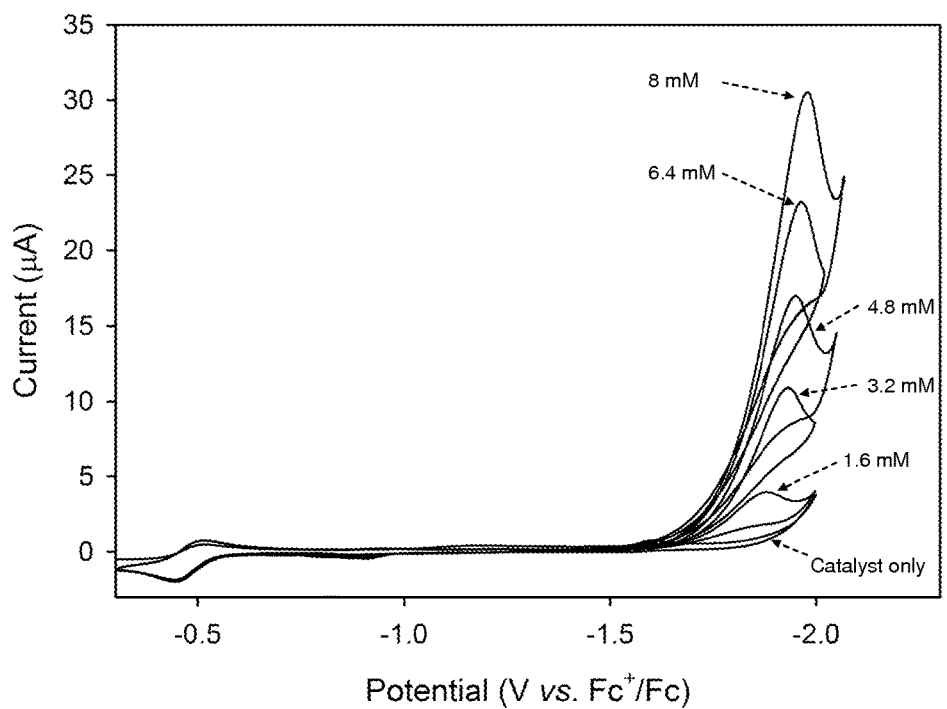
FIG. 20 shows cyclic voltammograms of complex A-1 (blank), with acetic acid 1.6, 3.2, 4.8, 6.4 and 8 mM in aqueous methanol solution (1 mM, scan rate=100 mV/s, 0.1 M n-Bu$_4$NPF$_6$, 1 mm vitreous carbon electrode, 299 K) under N$_2$, in Testing Example 3.
Figure 21:
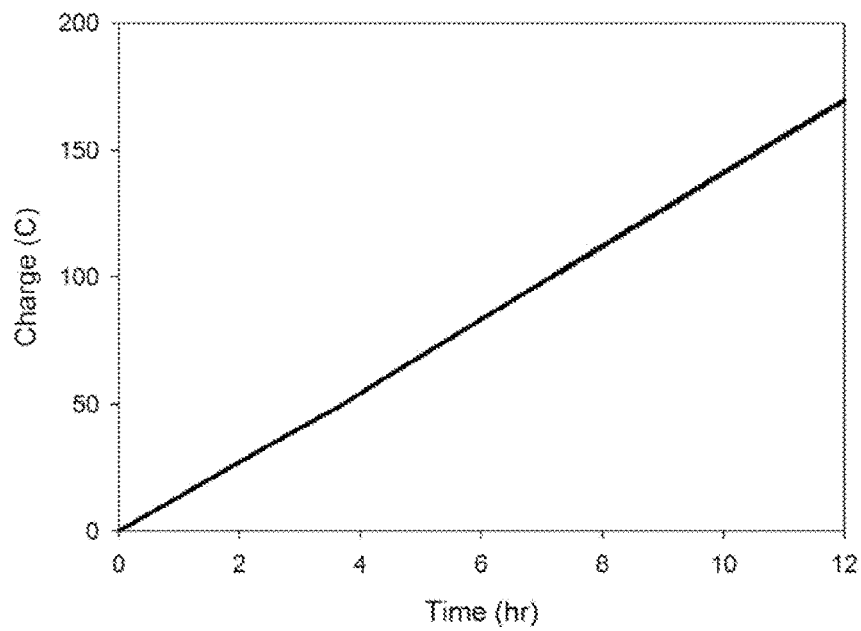
FIG. 21 shows the charge (Q)-time (t) plot at 297 K from controlled potential electrolysis of complex A-1 (0.5 mM) in an aqueous methanol solution under N$_2$, in Testing Example 3. The background reduction current of solution alone is subtracted. The potential was held at −1.8 V. Graphite rods (6.15 mm in diameter) were used as working and auxiliary electrodes. Reference electrode was a Ag wire pseudoelectrode.

The diiron dithiolate complex (complex A-1) produced in Example 1 was dissolved in aqueous methanol (95 wt %) to give a 0.5 mM solution. The solution was transferred to a 3-electrode electrochemical cell. In the absence of acid, cyclic voltammograms of complex A-1 revealed no observable redox process. To confirm that the catalyst (complex A-1) is responsible for catalysis in aqueous methanol solution, acetic acid was added by syringe to the solution. A catalytic wave was observed. The peak current of this wave shows linear increase with sequential increments of acids added in accompany with evolution of hydrogen gas. FIG. 20 displays that the catalytic wave grows in intensity as addition of acid (1.6, 3.2, 4.8, 6.4 and 8 mM) at 299 K with scan rate=100 mV/s, 0.1 M n-Bu$_4$NPF$_6$, 1 mm vitreous carbon electrode. Controlled-potential electrocatalysis of hydrogen production from the aqueous methanol solution was conducted in the aqueous methanol solution containing 0.5 mM of the diiron dithiolate complex (complex A-1) at 297 K (pK$_a$(MeOH)=15.5 in H$_2$O). The potential was held at −1.8 V. Graphite rods (6.15 mm in diameter) were used as working and auxiliary electrodes. Reference electrode was a Ag wire pseudoelectrode. The auxiliary and reference electrodes were placed in separated compartments with a fine porosity glass frit. FIG. 21 displays the charge (Q)-time (t) plot at 297 K under N$_2$, showing a linear plot during catalysis. No decomposition of catalyst was observed. The gas product was detected by GC, confirming the gas content being solely molecular hydrogen. Faraday yield is over 98%.

Testing Example 4

Products from the Reactions of Complex A-1

Isolation of complex 2 provided an opportunity to understand the protonation pathway involving a doubly reduced species ([(μ,κ$^2$-bdt)(μ-PPh$_2$)Fe$_2$(CO)$_5$]$^{2-}$) and to probe the role of the thiolate S site in protonation. Reaction of complex 2 with one equiv. of trifluoromethanesulfonic acid (HOTf) in dichloromethane solution generated a mono-protonated species [(μ-bdt)(μ-PPh$_2$)(μ-H)Fe$_2$(CO)$_5$] (complex A-8) which had four v$_{CO}$ bands at 2080 s, 2030 vs, 2013 s and 1983 m cm$^{-1}$. The shift of the IR bands to higher energy by ca. 75 cm$^{-1}$ suggested formation of the {Fe(μ-H)Fe} species with two Fe centers in the +2 oxidation state. The bridging hydride was identified at −14.08 ppm as a doublet (J$_{PH}$=51.5 Hz) using $^1$H NMR spectroscopy. Identification of the S-proton signal was assisted by employment of deuterium-substituted acids. The SD resonance but the Fe-deuteride was not observed from the reaction of complex 2 with 1 equiv. of DOTf at −40° C. Complex A-8 was a meta-stable species, which slowly converted to [(μ-bdt)Fe$_2$(CO)$_5$(PPh$_2$H)] (complex A-10) in solution, which was spectroscopically characterized.

Figure 22:
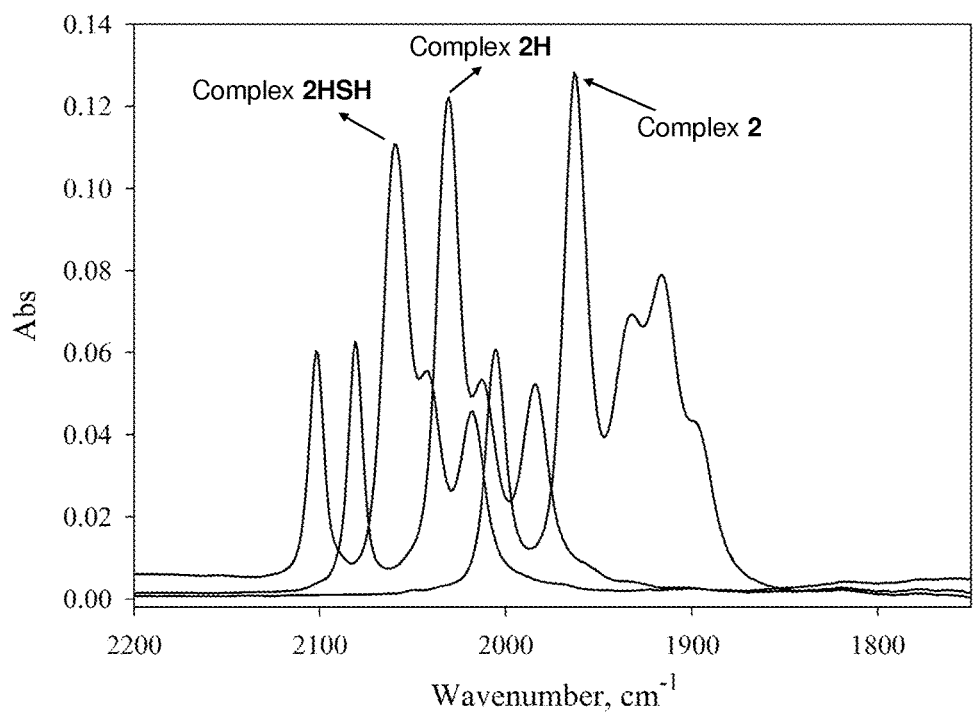
FIG. 22 shows the FTIR spectra of the complexes A-1, A-8 and A-9 in dichloromethane solution, in Testing Example 4. Complexes A-1, A-8 and A-9 are denoted as complexes 2, 2H and 2HSH, respectively in FIG.
Figure 23:
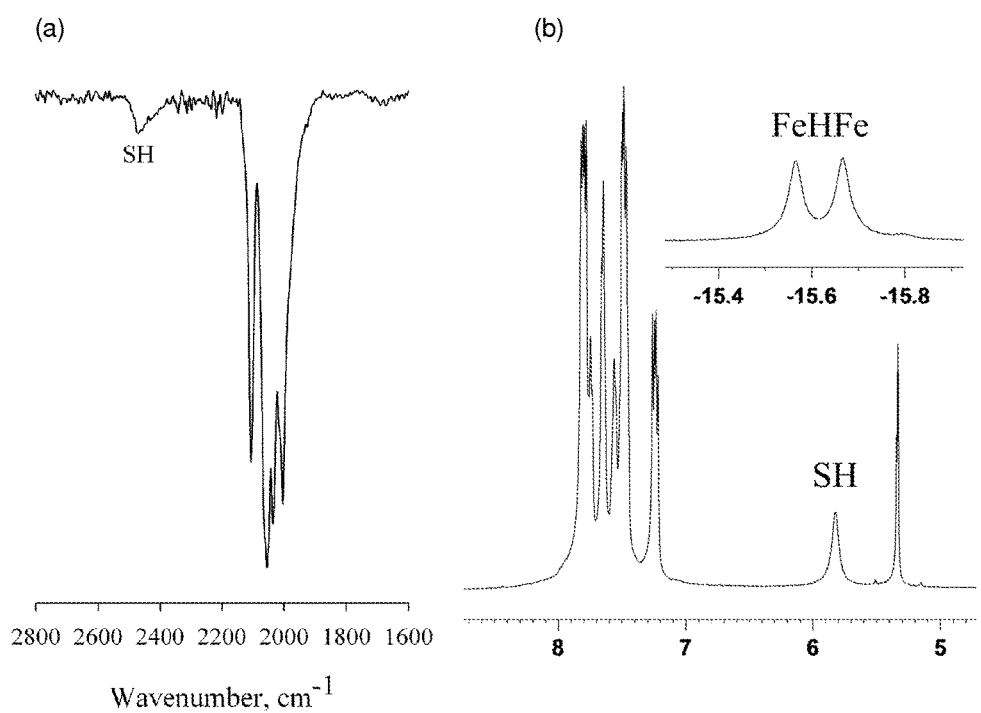
FIG. 23 shows (a) the IR spectrum of the complex A-9 in a KBr pellet, and (b) a selected region of the $^1$H-NMR spectra of the complex A-9 in dichloromethane solution, in Testing Example 4.

Consecutive protonation occurred for complex A-8 with addition of extra amounts of acids, which generated a 5-protonated orange species [(μ-bdtH)(μ-PPh$_2$)(μ-H)Fe$_2$(CO)$_5$]+(complex A-9). The IR profile, displayed in FIG. 22, remained unchanged upon 5-protonation and v$_{CO}$ of complex A-9 showed a positive shift of 29 cm$^{-1}$ as compared with that of complex A-8, which was characteristic of the protonated thiolate sulfur. A broad resonance at 5.83 ppm in the $^1$H NMR of A-9 was assigned to the proton on the terminal sulfur and the hydride was recorded as a doublet at −15.62 ppm (J$_{PH}$=50 Hz). Affirmative assignment of the sulfur proton was made from the results of the deuterium experiments. Peak broadness of the SD resonance (full width at half maximum (FWHM)=33.3 Hz) of A-9 at 263 K was larger than that of the FeDFe (FWHM=4.2 Hz). The SD signal becomes sharper as lower temperature was reached while the FeDFe did not reveal significant variation in broadness. It is suggested that the sulfur proton is labile and readily exchanges among the S site and the conjugate base of the acid. Deprotonation of A-9 to A-8 by solvent molecules readily occurred in THF solution. FIG. 23 shows (a) the IR spectrum of the complex A-9 in a KBr pellet, and (b) a selected region of the $^1$H-NMR spectra of the complex A-9.

To elucidate the protonation mechanism, the DFT calculation was carried out for exploration of the possible protonated structures. The optimized geometries and frequencies of complexes 2 and A-9 were in agreement with those obtained using X-ray crystallography and FTIR spectroscopy.

Figure 24:
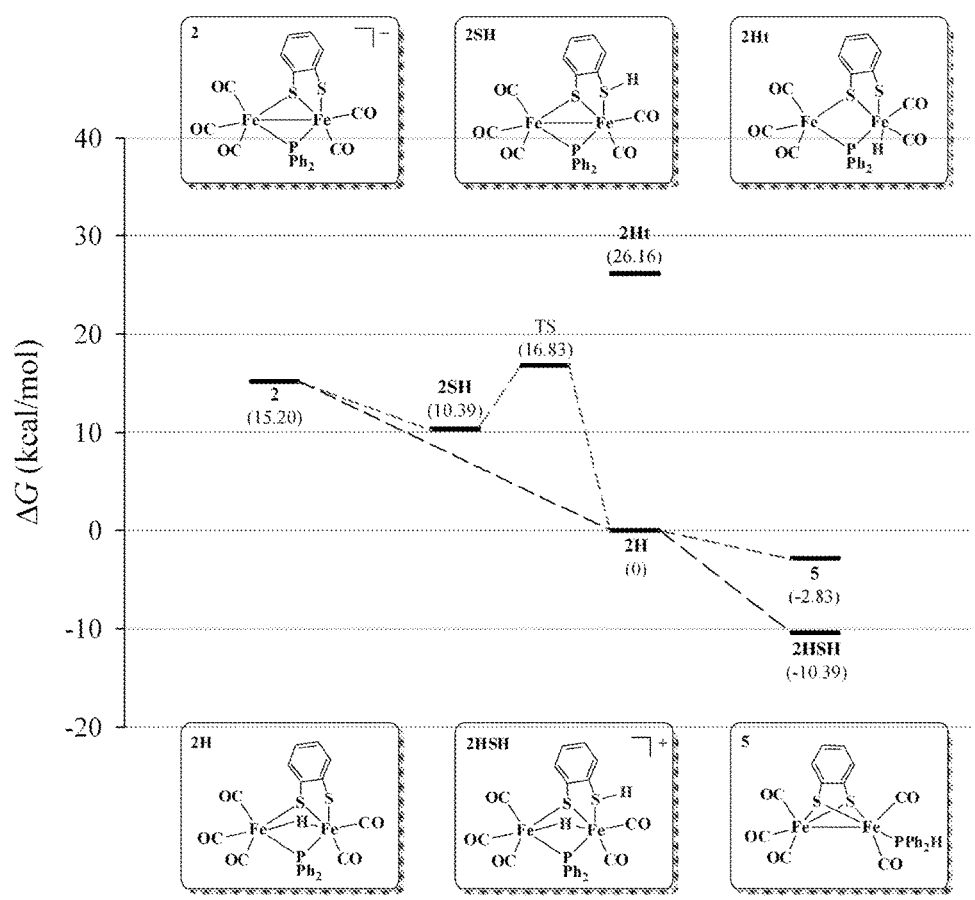
FIG. 24 shows a calculated free energy profile for all the possible species in the protonation processes, in Testing Example 4, wherein the long dash lines indicate the experimental reaction pathways, the short dash lines represent the different routes from the complex A-1 to the complex A-8, and the dot line indicates a tautomerization pathway. Complexes A-1, A-8, A-9, A-10, A-11 and A-12 are denoted as complexes 2, 2H, 2HSH, 5, 2Ht and 2SH, respectively in FIG.

FIG. 24 shows the free energy profile for the protonation pathway. The highest occupied molecular orbital (HOMO) of 2 significantly resides at both the diiron core and the terminal sulfur site, suggesting that they are susceptible to proton attacks. Free energy of the species resulting from sulfur-protonation as well as Fe-protonation was calculated, respectively. Single protonation onto the terminal sulfur site of complex 2 generates A-8 with a free energy lower than that of complex 2 by 4.81 kcal mol$^{-1}$. The [(μ-bdt)(μ-PPh$_2$)(t-H)Fe$_2$(CO)$_5$] (complex A-11, denoted as 2Ht in FIG. 24) species with a hydride terminally bound to the Fe site is destabilized by 10.96 kcal mol$^{-1}$. The most thermodynamically favored product is complex A-8 (the Fe-bridging hydride species) which is stabilized by 15.20 kcal mol$^{-1}$.

To validate the postulation of whether the S-protonation initially occurs along with the following proton relay in the Fee core or the formation of the A-8 species occurs directly, the transition state (TS) free energy for the conversion of the [(μ-Hbdt)(μ-PPh$_2$)Fe$_2$(CO)$_5$] (complex A-12, denoted as 2SH in FIG. 24) species to A-8 via an intramolecular pathway was calculated. An activation energy barrier of 6.44 kcal mol$^{-1}$ was estimated, which was larger than the energy difference between 2 and A-8. In accord with the low-temperature experimental data, the calculation results suggest that the route to A-8 via A-12 is thermodynamically unfavorable albeit its possibility cannot be exclusively eliminated.

Tautomerization of complex A-8 to [(t-bdt)Fe$_2$(CO)$_5$(PPh$_2$H)] (complex A-10, denoted as complex 5 in FIG. 24) is facilitated by that complex A-10 is further stabilized by 2.83 kcal mol$^{-1}$. The result was consistent with the experimental observation. A relative free energy of complex A-9 was computed to be 10.39 kcal mol$^{-1}$ less than that of complex A-8. The large ΔΔG value which is over 25 kcal mol$^{-1}$ is a driving force for instant protonation of complex 2 for generation of A-9 in the presence of free protons. The A-9 species is the end product throughout the protonation pathway. It is regarded as the ready-state species for the catalytic formation of molecular hydrogen by complex 2 in the presence of strong acids.

Complex 2 bearing an analog to the two-electron reduced species of [(μ-bdt)Fe$_2$(CO)$_6$] was synthesized to study the protonated products which are key intermediates in the catalytic mechanism for hydrogen formation. First protonation occurs onto the Fe—Fe vector to form the Fe bridging hydride species. Subsequent protonation onto the thiolate site occurs in the presence of additional acids. This step is to yield the most thermodynamically favored species according to the results of the DFT calculation. The first di-protonated [FeFe] hydrogenase model compound containing the S-proton was also successfully isolated and characterized. The results provide insights to elucidate the role of the Fe and S sites in coordination within the molecular catalyst at the reduced state in a pool of free protons. It is suggested that the thiolate sulfur acts a non-innocent site for accepting protons during the catalytic processes.

As compared to the existing complexes in the prior art, the iron-sulfur complexes provided herein have been proved to provide tremendous catalytic efficiency for hydrogen production because of their structural difference in which a terminal sulfur-containing ligand is coordinated to the Fe center.

3. An iron-sulfur complex, comprising: a compound having a structure of formula (I-2)
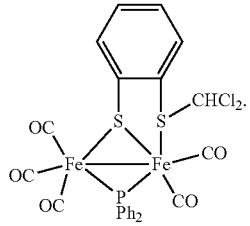
4. An iron-sulfur complex, comprising: a structure as below:
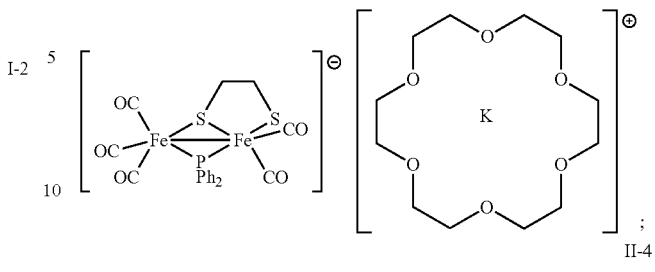
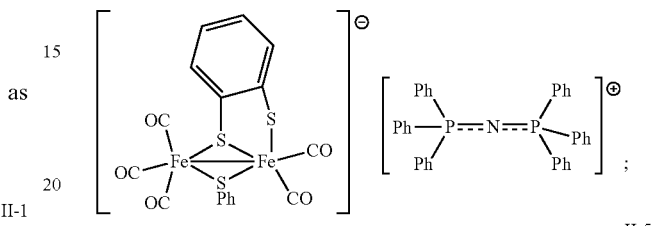
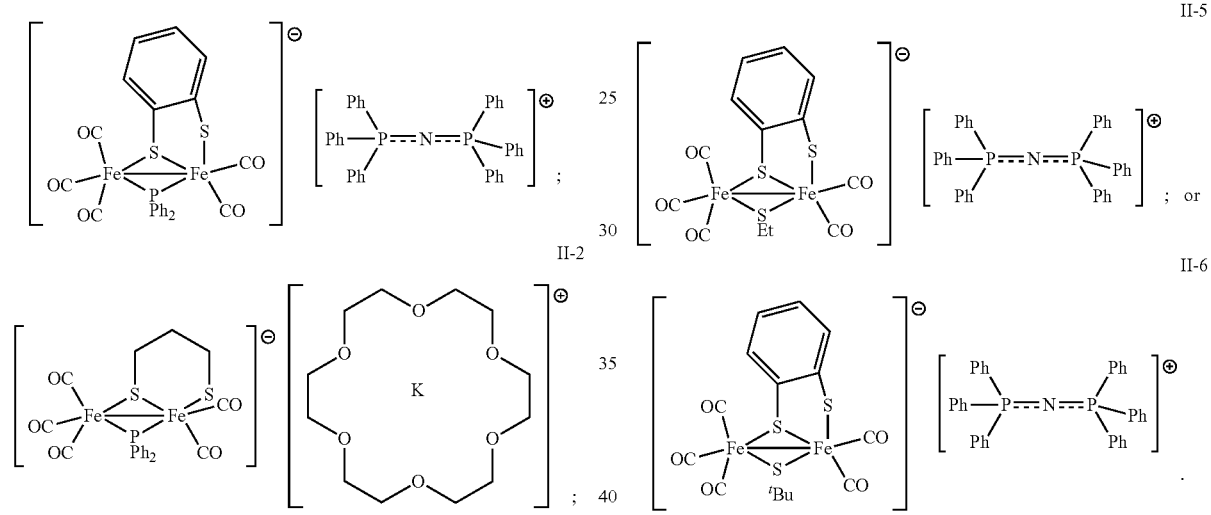

What is claimed is:

1. An iron-sulfur complex, comprising: a structure of formula (I)

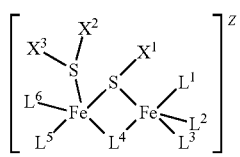

wherein

Z is a charge selected from an integer of −3 to +2;

L1, L2, L3, L5, or L6, X1, or X2 is a substituted or an unsubstituted functional group selected from the group consisting of: alkyl, alkenyl, alkynyl, phenyl, benzyl, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, orthocarbonate ester, carboxamide, primary amine, secondary amine, tertiary amine, primary ketimine, secondary ketimine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, phosphino, phosphono, phosphate, borono, boronate, borino, borinate and halogen;

X1 and X2 are substituents within one bridging group;

L4 is a bridging ligand selected from the group consisting of hydroxyl, cyanide, primary amide, secondary amide, sulfide, disulfide, sulfinyl, ethylthio (SEt), phenylthio (SPh), t-butylthio (S$^t$Bu), thiolate, phosphide, halide, oxide, nitride, borylene, boryl, boride and hydride;

X3 is a vacant site or a substituted or an unsubstituted functional group selected from the group consisting of: alkyl, alkenyl, alkynyl, phenyl, benzyl, hydroxyl, hydrogen, carbonyl, aldehyde, haloformyl, carbonate ester, carboxylate, carboxyl, ester, methoxy, hydroperoxy, peroxy, ether, hemiacetal, hemiketal, acetal, ketal, orthoester, orthocarbonate ester, carboxamide, primary amine, secondary amine, tertiary amine, primary ketimine, secondary ketimine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, phosphino, phosphono, phosphate, borono, boronate, borino, borinate and halogen.

2. An iron-sulfur complex, comprising: a structure of formula (II),

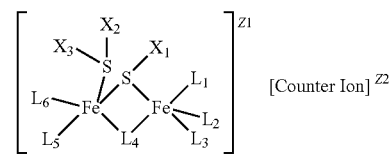

wherein

L1, L2, L3, L5, or L6 is a substituted or an unsubstituted functional group selected from the group consisting of: alkyl, alkenyl, alkynyl, phenyl, benzyl, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, orthocarbonate ester, carboxamide, primary amine, secondary amine, tertiary amine, primary ketimine, secondary ketimine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, phosphino, phosphono, phosphate, borono, boronate, borino, borinate and halogen;

X1 and X2 are substituents within one bridging group;

L4 is a bridging ligand selected from the group consisting of hydroxyl, sulfinyl, ethylthio (SEt), phenylthio (SPh), t-butylthio (S$^t$Bu), thiolate, phosphide, halide, oxide, nitride, borylene, boryl, and boride;

X3 is a vacant site or a substituted or an unsubstituted functional group selected from the group consisting of: alkyl, alkenyl, alkynyl, phenyl, benzyl, hydroxyl, hydrogen, carbonyl, aldehyde, haloformyl, carbonate ester, carboxylate, carboxyl, ester, methoxy, ether, hemiacetal, hemiketal, acetal, ketal, orthoester, orthocarbonate ester, carboxamide, imide, cyanate, and isocyanate;

Z1 and Z2 are individually a charge selected from an integer of −3 to +2 but not 0;

the [counter ion]$^{Z2}$ comprises: K$^+$(L7)$_n$, Na$^+$(L7)$_n$, Li$^+$(L7)$_n$, [n-Bu$_4$N]$^+$, [PPN]$^+$, or [CF$_3$SO$_3$]$^-$, L7 is a coordinating organic molecule, comprising: 18-crown-6-ether (1,4,7,10,13,16-hexaoxacyclooctadecane), 15-crown-5-ether (1,4,7,10,13-pentaoxacyclopentadecane), 12-crown-4-ether (1,4,7,10-tetraoxacyclododecane), or dibenzo-18-crown-6 (2,3,11,12-dibenzo-1,4,7,10,13,16-hexaoxacyclooctadeca-2,11-diene); or L7 is a coordinating solvent molecule of THF or MeCN; and n is an integer selected from +1 to +13.